(12) United States Patent
Biourge et al.

(10) Patent No.: US 11,771,113 B2
(45) Date of Patent: Oct. 3, 2023

(54) METHODS OF DIAGNOSING AND TREATING CHRONIC KIDNEY DISEASE

(71) Applicant: MARS, INCORPORATED, McLean, VA (US)

(72) Inventors: Vincent Biourge, Aimargues (FR); Jonathan Elliott, London (GB); Dirk Hendrik Nicolaas Van Den Broek, London (GB); Rosanne Ellen Jepson, London (GB); Yu-Mei Chang, London (GB)

(73) Assignee: MARS, INCORPORATED, McLean, VA (US)

( * ) Notice: Subject to any disclaimer, the term of this patent is extended or adjusted under 35 U.S.C. 154(b) by 493 days.

(21) Appl. No.: 16/615,317

(22) PCT Filed: May 31, 2018

(86) PCT No.: PCT/US2018/035385
§ 371 (c)(1),
(2) Date: Nov. 20, 2019

(87) PCT Pub. No.: WO2018/222865
PCT Pub. Date: Dec. 6, 2018

(65) Prior Publication Data
US 2020/0163363 A1    May 28, 2020

Related U.S. Application Data

(60) Provisional application No. 62/567,623, filed on Oct. 3, 2017, provisional application No. 62/513,396, filed on May 31, 2017.

(51) Int. Cl.
| | | |
|---|---|---|
| *A61K 33/06* | (2006.01) | |
| *A23K 20/24* | (2016.01) | |
| *A23K 50/40* | (2016.01) | |
| *A23K 10/00* | (2016.01) | |
| *G01N 33/84* | (2006.01) | |

(52) U.S. Cl.
CPC ............. *A23K 20/24* (2016.05); *A23K 10/00* (2016.05); *A23K 50/40* (2016.05); *G01N 33/84* (2013.01); *G01N 2800/347* (2013.01)

(58) Field of Classification Search
CPC .................................................... A61K 33/06
See application file for complete search history.

(56) References Cited

U.S. PATENT DOCUMENTS

| | | |
|---|---|---|
| 7,026,151 B2 | 4/2006 | Yamashita et al. |
| 8,058,015 B2 | 11/2011 | Kronenberg et al. |
| 8,481,690 B2 | 7/2013 | Murthy et al. |
| 8,637,482 B2 | 1/2014 | Feinstein et al. |
| 9,029,093 B2 | 5/2015 | Anderberg et al. |
| 9,091,684 B2 | 7/2015 | Yerramilli et al. |
| 9,500,660 B2 | 11/2016 | Martin et al. |
| 9,551,720 B2 | 1/2017 | Singbartl et al. |
| 9,669,010 B2 | 6/2017 | Archer |
| 10,087,449 B2 | 10/2018 | Ono |
| 10,339,464 B2 | 7/2019 | Martin |
| 2012/0077690 A1 | 3/2012 | Singbartl et al. |
| 2013/0122528 A1 | 5/2013 | Tyrell et al. |
| 2013/0130285 A1 | 5/2013 | Atkinson et al. |
| 2013/0210667 A1 | 8/2013 | Rovin et al. |
| 2014/0038203 A1 | 2/2014 | Arthur et al. |
| 2014/0194361 A1 | 7/2014 | Nicholas et al. |
| 2015/0104881 A1 | 4/2015 | Chen et al. |
| 2015/0178639 A1 | 6/2015 | Martin et al. |
| 2016/0033472 A1 | 2/2016 | Martin et al. |
| 2016/0144005 A1 | 5/2016 | Bernachon et al. |
| 2016/0187348 A1 | 6/2016 | Yerramilli et al. |
| 2016/0320410 A1 | 11/2016 | Bobadilla et al. |
| 2017/0315134 A1 | 11/2017 | Anderberg et al. |
| 2018/0055885 A1 | 3/2018 | Jain et al. |

FOREIGN PATENT DOCUMENTS

| | | |
|---|---|---|
| EP | 3112871 A1 | 1/2017 |
| EP | 3065559 B1 | 1/2019 |
| JP | 2012-519201 A | 8/2012 |
| WO | WO 2012/100991 A1 | 8/2012 |
| WO | WO 2014/092158 A1 | 6/2014 |
| WO | WO 2016/133909 A1 | 8/2016 |
| WO | WO 2020/018463 A1 | 1/2020 |

OTHER PUBLICATIONS

Wyskida et al., Journal of Renal Nutrition, 2012, 22(1): 19-25.*
Geiger et al. et al., Clin Kidney J, 2012, 5, suppl 1: i25-i38.*
Anonymous: "Chronic Diagnosing, Staging, and Treating Chronic Kidney Disease in Dogs and Cats," Dec. 5, 2019 (Dec. 5, 2019), XP055836702, Retrieved from the Internet: URL:https://web.archive.org/web/20191205020609if/https://www.idexx.com/files/iris-pocket-guide-2.pdf.
Anonymous: "Recurrent neural network—Wikipedia," May 17, 2020 (May 17, 2020), XP055836856, Retrieved from the Internet: URL:https://en.wikipedia.org/w/index.php?title=Recurrentneuralnetwork&oldid=9572466.
Hand et al., "Chapter 19—Renal Disease. In: Small Animal Clinical Nutrition, 4th ed.," Dec. 31, 2000, pp. 563-604.
Anonymous: Amylase: eCiinpath, eClinPath.com, Jun. 5, 2019 (Jun. 5, 2019), XP055837398, Retrieved from the Internet: URL:https://web.archive.org/web/20190605192816/https://eclinpath.com/chemistry/pancreas/amylase/.

(Continued)

*Primary Examiner* — Rei Tsang Shiao
(74) *Attorney, Agent, or Firm* — Baker Botts L.L.P.

(57) ABSTRACT

The presently disclosed subject matter relates to methods of diagnosing and treating chronic kidney disease (CKD) in an animal, comprising determining the amount of magnesium in a sample of the animal and providing the animal with a treatment regimen. In certain embodiments, the treatment regimen comprises administering an effective amount of magnesium.

15 Claims, 9 Drawing Sheets

(56) References Cited

OTHER PUBLICATIONS

Brownlee Jason, "A Gentle Introduction to Threshold-Moving for Imbalanced Classification," Feb. 12, 2020 (Feb. 12, 2020), XP055837437, Retrieved from the Internet: URL:https://web.archive.org/web/20200311074021/https://machinelearningmastery.com/threshold-moving-for-imbalanced-classification/.

Carpenter et al., "Multiple Imputation of Quantitative Data: Carpenter/Multiple Imputation and its Application," In: "Multiple Imputation and its Application : Carpenter/Multiple Imputation and its Application," 2013 John Wiley & Sons, Ltd, Chichester, UK, pp. 75-89.

International Search Report and Written Opinion dated Sep. 16, 2021 in International Application No. OCT/US2021/035219.

Bressendorff et al., "Oral Magnesium Supplementation in Chronic Kidney Disease Stages 3 and 4: Efficacy, Safety, and Effect on Serum Calcification Propensity—A Prospective Randomized Double-Blinded Placebo-Controlled Clinical Trial," Kidney International Reports, 2:380-389 (2017).

De Francisco et al., "Magnesium—its role in CKD," Nefrologia 33(3):389-399 (2013).

Deekajorndech, "A Biomarker for Detecting Early Tubulointerstitial Disease and Ischemia in Glomerulonephropathy," Renal Failure, 29:1013-1017 (2007).

Geddes et al., "Relationship between Plasma Fibroblast Growth Factor-23 Concentration and Survival Time in Cats with Chronic Kidney Disease," J Vet Intern Med, 29:1494-1501 (2015).

International Search Report and Written Opinion dated Jul. 24, 2018 in International Application No. PCT/US2018/035385, 16 pages.

Miura et al., "Role of Hypomagnesemia in Chronic Cyclosporine Nephropathy," Transplantation, 73(3):340-347 (2002).

Musso, "Magnesium metabolism in health and disease," International Urology and Nephrology, 41:357-362 (2009).

Van Laecke et al., "Hypomagnesemia and the Risk of Death and GFR Decline in Chronic Kidney Disease," The American Journal of Medicine, 126:825-831 (2013).

Dickerson, et al., Chapter 20, Coordination Chemistry, Chemical Principles: Third Edition—1982—pp. 734-738 [with English translation].

Fedorov, "On the problem of determining microelements in human blood serum," Analytics and Control, Mar. 2005, 358-366, T.9, No. 4 (with English abstract).

Kharkevich, "Dependence of Pharmacotherapeutic Action On Drug Properties And Pattern Of Use," Pharmacology, Moscow, Medicine, 1987, pp. 47-48 [with English translation].

Elin, "Assessment of magnesium status for diagnosis and therapy," Magnesium Research 23(4):S194-S198 (2010).

Geiger et al., "Magnesium in disease," Clinical Kidney Journal 5[Suppl 1 ]:i25-i38 (2012).

Ishimura et al., "Serum magnesium concentration is a significant predictor of mortality in maintenance hemodialysis patients," Magnesium Research 20(4):237-244 (2007).

Sakaguchi et al., "Magnesium modifies the association between serum phosphate and the risk of progression to end-stage kidney disease in patients with non-diabetic chronic kidney disease," Kidney Int 88:833-842 (2015).

Nakamura et al., "Influence of the magnesium oxide as laxative on serum magnesium level in the renal function disorder patients," Jpn J Nephrol Pharmacother, 2(1):3-9 (2013) [with English abstract].

Nakano et al., "Combined Use of Vitamin D Status and FGF23 for Risk Stratification of Renal Outcome," Clin J Am Soc Nephrol, 7:810-819 (2012).

Bala et al., A Literature Review on Kidney Disease Prediction using Data Mining Classification Technique, International Journal of Computer Science and Mobile Computing, vol. 3, Issue 7, Jul. 2014, 960-967.

Bijsmans et al., Changes in Systolic Blood Pressure over Time in Healthy Cats and Cats with Chronic Kidney Disease, J. Vet. Intern. Med., May/Jun. 2015, 855-861, 29(3).

Bradley, et al., Predicting early risk of chronic kidney disease in cats using routine clinical laboratory tests and machine learning, J. Vet. Intern. Med., Sep. 26, 2019, 1-13, 33-6.

Brown, et al., Chronic Kidney Disease in Aged Cats: Clinical Features, Morphology, and Proposed Pathogeneses, Veterinary Pathology, Mar. 2016;53(2):309-326.

Cannon, Diagnosis and investigation of chronic kidney disease in cats, In Practice, Nov. 7, 2016, pp. 2-9, vol. 38, Suppl. 3.

Chakrabarti et al., Clinicopathological Variables Predicting Progression of Azotemia in Cats with Chronic Kidney Disease, J. Vet. Intern. Med., Jan. 2012, 275-281, 26.

Chen et al., Plasma indoxyl sulfate concentration predicts progression of chronic kidney disease in dogs and cats, The Veterinary Journal, Feb. 2018, 33-39 (Abstract Only, 2 pgs.), 232.

Conroy et al., Chronic kidney disease in cats attending UK practices—Projects—VetCompass, https://web.archive.org/web/20160412192727/https://www.rvc.ac.uk/vetcompass/projects/chronic-kidney-disease-in-cats-attending-uk-practices, Sep. 2015, 2 pgs.

Elliott et al., Dietary therapy for feline chronic kidney disease, Encyclopedia of feline clinical nutrition, 2nd edition, Chapter 12, 2015, 36 pgs., N/A.

Finch et al., Development of an estimated glomerular filtration rate formula in cats, J. Vet. Intern. Med., Nov./Dec. 2018, 1970-76, 32(7).

Finch et al., Fibroblast growth factor 23 (FGF-23) concentrations in cats with early nonazotemic chronic kidney disease (CKD) and in healthy geriatric cats, J. Vet. Intern. Med., Mar.-Apr. 2013, 227-233, 27.

Finch et al., Glomerular filtration rate estimation by use of a correction formula for slope-intercept plasma iohexol clearance in cats, American Journal of Veterinary Research, Dec. 2011, 1652-1659 (Abstract Only, 2 pgs.)., 72(12).

Finch et al., Prediction Formulae for Fat Free Mass (FFM) and Estimated Clomerular Filtration Rate (eGFR) in Cats, J. Vet. Intern. Med., Nov./Dec. 2010, 1548 (Abstract Only, 1 pg.), 24(6).

Finch et al., Risk Factors for Development of Chronic Kidney Disease in Cats, Journal of Veterinary Internal Medicine, Mar. 2016, 602-10, 30(2).

Foster, Update on Mineral and Bone Disorders in Chronic Kidney Disease, Vet Clin North Am Small Anim Pract, Nov. 2016, 1131-49, 46(6).

Frandsen, Machine Learning for Disease Prediction, BYU Scholars Archive, Jun. 1, 2016, 68 pages, Thesis, Brigham Young University.

Ghys, et al., Cystatin C: A new Renal Marker and Its Potential Use in Small Animal Medicine, J. Vet. Intern. Med., Jul.-Aug. 2014, 1152-1164, 28(4).

Giorgino, Computing and Visualizing Dynamic Time Warping Alignments in R: The dtw Package, Journal of statistical Software, Aug. 2009, 1-24, 31(7).

Granitto, et al., Recursive feature elimination with random forest for PTR—MS analysis of agroindustrial products, Chemometrics and Intelligent Laboratory Systems, Sep. 15, 2006, 83-90, 83-2.

Grauer, Iris International Renal Interest Society, downloaded from http://www.iris-kidney.com/education/utility_creatine_early_diagnosis_ckd.html on Jun. 5, 2019, 4 pgs.

Grauer, Use of Serum Creatinine & Symmetric Dimethylarginine, Early Diagnosis of Chronic Kidney Disease in Dogs & Cats, Today's Veterinary Practice, tvpjournal.com, (Mar./Apr. 2016), 68-72.

Hall et al., Comparison of Serum Concentrations of Symmetric Dimethylarginine and Creatinine as Kidney Function Biomarkers in Cats with Chronic Kidney Disease, J. Vet. Intern. Med., Nov.-Dec. 2014, 1676-1683, 28-6.

IRIS International Renal Interest Society, Grading of Acute Kidney Injury (2013), 7 pgs.

IRIS International Renal Interest Society, Iris Staging of CKD, 9 pgs. (2015).

Jepson et al., Evaluation of mass spectrometry of urinary proteins and peptides as biomarkers for cats at risk of developing azotemia, American Journal of Veterinary Research, Feb. 2013, 333-342 (Abstract Only, 1 pg.), 74(2).

Jepson et al., Evaluation of Predictors of the Development of Azotemia in Cats, J. Vet. Intern. Med., Jun. 2009, 806-813, 23-4.

(56) References Cited

OTHER PUBLICATIONS

Lefebvre, Literature Review—Epidemiology of Feline Chronic Kidney Disease, Banfield Pet Hospital, BARK, Putting Knowledge into Practice (Oct. 2011), 12 pgs.

Minimaxscaler, http://scikit-learn.org/stable/modules/generated/sklearn.preprocessing.MinMaxScaler, Downloaded from the internet, Apr. 3, 2018, 5 pgs., N/A.

Norouzi et al., Predicting Renal Failure Progression in Chronic Kidney Disease Using Integrated Intelligent Fuzzy Expert System, Computational and Mathematical Methods in Medicine, 2016 (Dec. 2015), 1-9, Article ID 6080814.

O'Neill et al., Longevity and mortality of cats attending primary-care veterinary practices in England, J. Feline Med. Surg., Feb. 2015, 125-33, 17(2).

O'Neill et al., Prevalence of disorders recorded in cats attending primary-care veterinary practices in England, The Veterinary Journal, Nov. 2014, 286-291, 202(2).

Sharma et al., Performance Based Evaluation of Various Machine Learning Classification Techniques for Chronic Kidney Disease Diagnosis, ternational Journal of Modern Computer Science (IJMCS), Jun. 2016, 11-16, 4(3).

Srivastava, Dropout: a simple way to prevent neural networks from overfitting, Journal of Machine Learning Research, Jun. 2014, 1929-1958, 15(1).

Stekhoven et al., MissForest—nonparametric missing value imputation for mixed-type data, Bioinformatics, Jan. 2012, 112-118, 28(1).

Syme, CKD Early Diagnosis, IRIS International Renal Interest Society, downloaded on Jun. 5, 2019 from http://www.iris-kidney.com/education/early_diagnosis.html (2016), 4 pgs.

Tan, Neighbor-weighted k-nearest neighbor for unbalanced text corpus, Expert Systems with Applications, May 2005, 667-671, 28(4).

Van Hoek et al., Short- and long-term follow-up of glomerular and tubular renal markers of kidney function in hyperthyroid cats after treatement with radioiodine, Domestic Animal Endocrinology, Jan. 1, 2009, pp. 45-56, vol. 36, No. 1.

Xiao et al., Comparison and development of machine learning tools in the prediction of chronic kidney disease progreession, J. Transl. Med., Apr. 2019, 13 pgs, 17(119).

Yadollahpour, Applications of Expert Systems in Management of Chronic Kidney Disease: A Review of Predicting Techniques, Oriental Journal of Computer Science & Technology, Aug. 2014, 306-315, 7(2).

Fritsch et al., "Acceptance and effects of a therapeutic renal food in pet cats with chronic kidney disease," Vet Rec Open 2:e000128 (2015) 7 pgs.

Geddes et al., "The Effect of Feeding a Renal Diet on Plasma Fibroblast Growth Factor 23 Concentrations in Cats with Stable Azotemic Chronic Kidney Disease," J Vet Intern Med 27:1354-1361 (2013).

Hill's Pet Prescription Diet k/d Feline Renal Health with Chicken (https://web.archive.org/web/2o170518071812/https://www.myvet.co.nz/hills-feline-kd.html) 3 pgs.

Hill's Pet Prescription Diet k/d Feline Renal Health, 1 pg. (2015).

Katsuyuki et al., "Role of Hypomagnesemia in Chronic Cyclosporine Nephropathy," Transplantation 73(3):340-347 (2002).

Purina Pro Plan Veterinary Diets NF Kidney Function—feline and canine formula, 6 pgs. (2015).

Rayne Clinical Nutrition, Restrict-CKD Canine wet diet, 4 pgs. (2016).

Royal Canin Product Guide, 10 pgs. (2015).

\* cited by examiner

METHODS OF DIAGNOSING AND TREATING CHRONIC KIDNEY DISEASE

CROSS-REFERENCE TO RELATED APPLICATIONS

This patent application is a U.S. National Stage Patent Application under 35 U.S.C. § 371 of International Patent Application No. PCT/US2018/035385, filed May 31, 2018, which claims priority to U.S. Provisional Patent Application Ser. No. 62/513,396 filed May 31, 2017 and to U.S. Provisional Patent Application Ser. No. 62/567,623 filed Oct. 3, 2017, the contents of each of which are hereby incorporated by reference in their entireties, and to each of which priority is claimed.

FIELD OF THE INVENTION

The presently disclosed subject matter relates to methods of diagnosing and treating chronic kidney disease (CKD) in an animal, such as a domestic animal or a pet (e.g., a cat or a dog).

BACKGROUND OF THE INVENTION

Chronic kidney disease (CKD), also known as chronic renal disease or chronic renal failure, is a progressive loss in renal function over a period of months or years. CKD can be caused by a variety of conditions and mechanisms, and affects both humans and other mammals, in particular cats. Renal function in geriatric cats progressively declines over time, leading to end-stage disease.

In animals which suffer from renal disease, several blood indices are used to determine the severity of the disease. These indices include blood urea nitrogen (BUN), phosphorus, fibroblast growth factor 23 (FGF23), parathyroid hormone (PTH) and creatinine. BUN, phosphorus, and creatinine levels in the bloodstream increase during the course of renal failure because damage to the kidney of the animal makes the kidney inadequate to filter waste products. Phosphorus retention occurs early in chronic kidney disease, resulting in elevated serum concentrations of FGF23 and PTH. Increased serum concentrations of FGF23 and PTH also contribute to progression of kidney disease and can further contribute to bone and mineral disorders in chronic kidney disease. Different approaches to treat or delay the progression of CKD have been attempted, including dietary therapies, the control of hypertension and hemodialysis. Current dietary therapies include decreasing the amount of dietary protein and phosphorus. However, such diets can result in other problems as the animal's protein needs are unmet. Accordingly, there remains a need in the art for pet food compositions which can treat or delay the progression of CKD.

A scheme for staging CKD in cats and dogs has been developed by the International Renal Interest Society (IRIS) (www.iris-kidney.com; see also Elliott et al., Dietary therapy for feline chronic kidney disease, Encyclopedia of feline clinical nutrition, 2nd edition, 2015). The basis for the staging system is the plasma creatinine concentration. This staging system is broadly adopted, however, there remains a need in the art for methods of monitoring other aspects of the progression of CKD and optimizing the treatment options.

Hyperphosphatemia is a well-documented sequela of CKD in cats,[1-5] and has been associated with increased risks for death and progression of azotemia.[6-8] Phosphate retention results from inability of the kidney to excrete sufficient phosphate to balance dietary intake.[9,10] Actions of the body to maintain normophosphatemia result in secondary renal hyperparathyroidism and FGF-23 excess.[10] These hormonal derangements prevent overt hyperphosphatemia in the early stages of CKD,[11] but are thought to contribute to bone pathology and soft tissue calcification which together with disturbed calcium-phosphate homeostasis comprise CKD-mineral and bone disorder (CKD-MBD).[10,12,13] FGF-23 itself is a strong predictor of survival and progression in cats with CKD.[5] Dietary phosphate restriction is the mainstay of management of CKD in cats, and has been shown to reduce plasma phosphate, FGF-23 and PTH concentrations and improve survival.[14-18]

Recently, there has been increased interest in the role of magnesium in human CKD-MBD. In addition to being an essential mineral for numerous intracellular processes,[19] magnesium is thought to be an inhibitor of vascular calcification[20-22] and release of profibrotic cytokines.[23] Hypomagnesemia was identified as a risk factor for mortality,[24-28] and possibly kidney function decline in human CKD patients.[23,24] Serum total magnesium concentration (tMg) furthermore appeared to modify the risks associated with hyperphosphatemia in humans with CKD, as high phosphate was only associated with higher risks of mortality[27] and progression to end-stage renal disease[23] in patients with lower tMg. Interestingly, magnesium may be involved in FGF-23 regulation, because an inverse association between these two variables was observed in human CKD patients on hemodialysis,[29] and FGF-23 concentrations were increased in rodents fed a magnesium deficient diet.[30,31]

Little is known about the role of magnesium in feline CKD-MBD. A study among cats with azotemic CKD found significantly increased plasma tMg in end-stage disease, whilst low plasma tMg were observed in up to 25% of cats with earlier stages of CKD.[3] Neither the prognostic significance of magnesium status, nor the relationship between magnesium and FGF-23 have been examined in cats with CKD. Thus, there remains a need for further investigation in this regard.

SUMMARY OF THE INVENTION

In certain non-limiting embodiments, the presently disclosed subject matter provides for methods of treating or delaying progression of chronic kidney disease (CKD) in an animal in need thereof. In certain embodiments, the method comprises: determining an amount of magnesium in a blood sample of the animal; comparing the amount of magnesium to a predetermined reference value; wherein the predetermined reference value is based on an average magnesium level in blood in a control population; and providing the animal with a composition comprising magnesium or salt thereof to treat the animal if the amount of magnesium is below the predetermined reference value.

In certain non-limiting embodiments, the presently disclosed subject matter provides for methods of treating or delaying progression of CKD in an animal in need thereof, wherein the animal has a magnesium deficiency compared to a predetermined reference value. In certain embodiments, the method comprises: administering a composition comprising an effective amount of magnesium or salt thereof, and wherein the predetermined reference value is based on an average magnesium level in blood in a control population.

In certain non-limiting embodiments, the presently disclosed subject matter provides for methods of treating or delaying progression of CKD in an animal in need thereof.

In certain embodiments, the method comprises: determining an amount of magnesium in a blood sample of the animal; comparing the amount of magnesium to predetermined reference values; wherein the predetermined reference values are based on average magnesium levels in blood in a control population; and providing the animal with a treatment regimen if the amount of magnesium is below a first predetermined value or above a second predetermined reference value.

In certain non-limiting embodiments, the presently disclosed subject matter provides for methods of diagnosing and treating an animal at risk for CKD. In certain embodiments, the method comprises: obtaining a blood sample from the animal; determining an amount of magnesium in the blood sample of the animal; comparing the amount of magnesium to predetermined reference values; wherein the predetermined reference values are based on average magnesium levels in blood in a control population; diagnosing the animal as being at risk for the CKD if the amount of magnesium is below a first predetermined value or above a second predetermined reference value; and providing the animal with a treatment regimen if the amount of magnesium is below a first predetermined value or above a second predetermined reference value.

In certain embodiments, the methods provided in the presently disclosed subject matter further comprise the steps of determining an amount of FGF23 in the blood sample of the animal; comparing the amount of FGF23 to a third predetermined reference value; and wherein the predetermined reference value is based on an average FGF23 level in blood in a control population, and wherein a higher FGF23 level compared to the second predetermined reference value indicates a higher likelihood of effective treatment.

In certain embodiments, the treatment regimen provided in the presently disclosed subject matter comprises at least one treatment regimen selected from the group consisting of administering a composition comprising an effective amount of magnesium or a salt thereof, reducing phosphate intake, reducing protein intake, administering polyunsaturated fatty acids, administering a phosphate binder therapy, administering potassium, reducing dietary sodium intake, and combinations thereof.

In certain embodiments, the treatment regimen provided in the presently disclosed subject matter comprises at least one treatment regimen selected from the group consisting of a dietary therapy, hemodialysis, renal replacement therapy, withdrawal of kidney damaging compounds, kidney transplantation, delaying or avoiding kidney damaging procedures, modifying diuretic administration, and combinations thereof.

In certain embodiments, the methods provided in the presently disclosed subject matter further comprises: determining an amount of at least one further biomarker selected from the group consisting of phosphate, creatinine, blood urine nitrogen (BUN) and parathyroid hormone (PTH) in the blood sample, and comparing the amount of the at least one further biomarker to a fourth predetermined reference value, wherein the amount of phosphate, creatinine, blood urine nitrogen (BUN) and/or parathyroid hormone (PTH) being above the fourth predetermined reference value indicates a higher likelihood of effective treatment.

In certain embodiments, the methods provided in the presently disclosed subject matter further comprise maintaining the animal on the composition for a sufficient period of time to reduce the amount of FGF23 in the animal.

In certain embodiments, the amount of magnesium in the blood sample is less than about 50% of the average amount of magnesium in blood in a control population.

In certain embodiments, the amount of FGF23 or the further biomarkers in the blood sample is at least about 150% of the average amount of FGF23 or the further biomarkers in blood in a control population.

In certain embodiments, the methods provided in the presently disclosed subject matter further comprises: determining blood pressure of the animal, comparing the blood pressure to a fifth predetermined reference value, and administrating a prevention or treatment regimen of hypertension if the blood pressure is higher than the fifth predetermined reference value.

In certain embodiments, the magnesium is in a magnesium coordination complex.

In certain embodiments, the treatment regimen is administering a composition comprising an effective amount of magnesium or a salt thereof.

In certain embodiments, the amount of the magnesium is between about 50 mg/1000 Kcal and about 500 mg/1000 Kcal.

In certain embodiments, the composition comprises magnesium is provided to the animal at least once a day.

In certain embodiments, the amount of magnesium is determined by mass spectrometry, fluorescence, or luminescence.

In certain embodiments, the amount of FGF23 is determined by an enzyme-linked immunosorbent assay (ELISA).

In certain embodiments, the animal is a companion animal such as a dog or a cat.

In certain non-limiting embodiments, the presently disclosed subject matter provides for pet food compositions comprising an effective amount of magnesium or salt thereof for treating or delaying the progression of CKD in an animal in need thereof.

In certain embodiments, the amount of the magnesium is between about 50 mg and about 100 mg per daily serving or unit dosage.

In certain embodiments, the amount of the magnesium is no more than about 0.25% weight by weight of the pet food composition.

In certain non-limiting embodiments, the presently disclosed subject matter provides for use of magnesium for treating or delaying progression of CKD in an animal in need thereof, wherein the animal has a magnesium deficiency compared to a predetermined reference value, and wherein the predetermined reference value is based on an average magnesium level in blood in a control population.

In certain non-limiting embodiments, the presently disclosed subject matter provides for use of magnesium levels in blood as a biomarker to predict and/or quantify chronic kidney disease in an animal, wherein the magnesium levels compared to a predetermined reference value provide a basis for a need for dietary intervention to treat the chronic kidney disease in the animal in need thereof.

In certain non-limiting embodiments, the presently disclosed subject matter provides for methods of diagnosing chronic kidney disease (CKD) in an animal comprising: determining an amount of magnesium in a blood sample of the animal; comparing the amount of magnesium to predetermined reference values; wherein the predetermined reference values are based on an average magnesium level in blood in a control population; and wherein an amount of magnesium below a first predetermined value or above a second predetermined reference value indicates presence or likelihood of CKD.

DETAILED DESCRIPTION OF THE INVENTION

Figure 1:
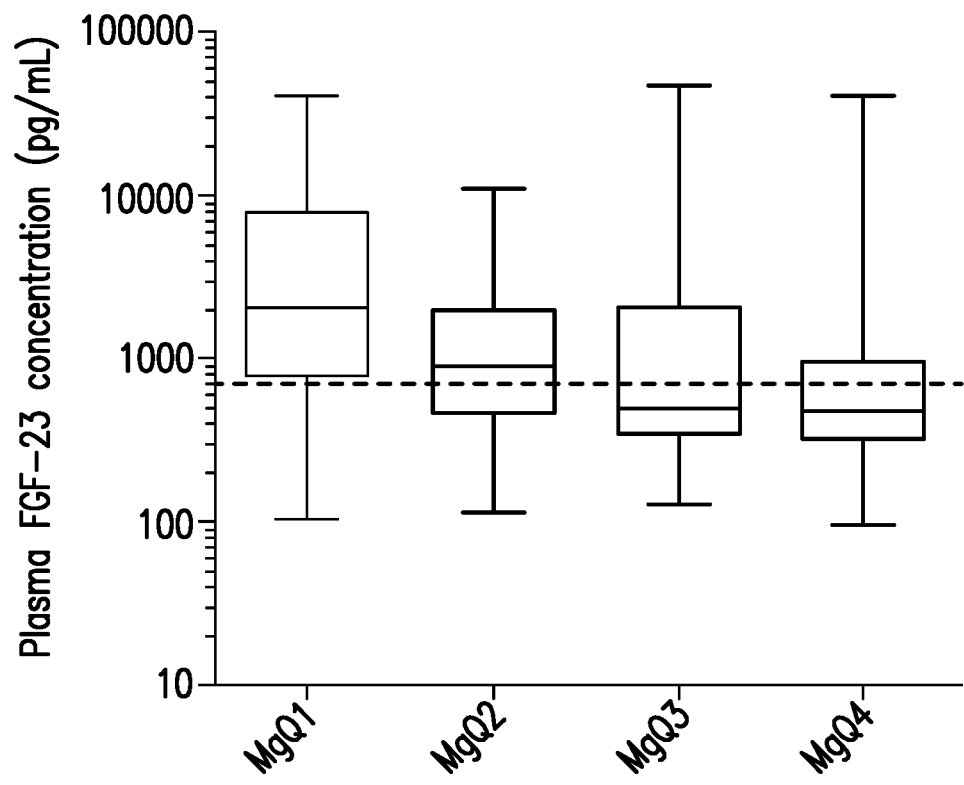
FIG. 1 shows plasma FGF-23 concentrations in cats with azotemic CKD IRIS stage 2-3 categorized in quartiles according to plasma total magnesium concentration.

To date, there remains there remains a need for pet food compositions for treating CKD and for methods of monitoring the progression of CKD and optimizing the treatment regimens. The present application relates to biomarkers for diagnosing CKD in an animal, including, but are not limited to, magnesium and FGF23, and methods for treating CKD using the same. The present application also provides pet food products comprising an effective amount of magnesium for treating CKD. For clarity and not by way of limitation, the detailed description of the presently disclosed subject matter is divided into the following subsections:

1. Definitions;
2. Biomarkers;
3. Treatment methods; and
4. End products.

1. Definitions

The terms used in this specification generally have their ordinary meanings in the art, within the context of this invention and in the specific context where each term is used. Certain terms are discussed below, or elsewhere in the specification, to provide additional guidance to the practitioner in describing the methods and compositions of the invention and how to make and use them.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

The term "effective treatment" or "effective amount" of a substance means the treatment or the amount of a substance that is sufficient to effect beneficial or desired results, including clinical results, and, as such, an "effective treatment" or an "effective amount" depends upon the context in which it is being applied. In the context of administering a composition to reduce the risk of CKD, and/or administering a composition to treat or delay the progression of CKD, an effective amount of a composition described herein is an amount sufficient to treat and/or ameliorate CKD, as well as decrease the symptoms and/or reduce the likelihood of CKD. An effective treatment described herein is a treatment sufficient to treat and/or ameliorate CKD, as well as decrease the symptoms and/or reduce the likelihood of CKD. The decrease can be a 10%, 20%, 30%, 40%, 50%, 60%, 70%, 80%, 90%, 95%, 98% or 99% decrease in severity of symptoms of CKD, or likelihood of CKD. An effective amount can be administered in one or more administrations. A likelihood of an effective treatment described herein is a probability of a treatment being effective, i.e., sufficient to treat and/or ameliorate CKD, as well as decrease the symptoms.

As used herein, and as well-understood in the art, "treatment" is an approach for obtaining beneficial or desired results, including clinical results. For purposes of this subject matter, beneficial or desired clinical results include, but are not limited to, alleviation or amelioration of one or more symptoms, diminishment of extent of disease, stabilized (i.e., not worsening) state of disease, prevention of disease, delay or slowing of disease progression, and/or amelioration or palliation of the disease state. The decrease can be a 10%, 20%, 30%, 40%, 50%, 60%, 70%, 80%, 90%, 95%, 98% or 99% decrease in severity of complications or symptoms. "Treatment" can also mean prolonging survival as compared to expected survival if not receiving treatment.

The term "pet food" or "pet food composition" or "pet food product" or "final pet food product" means a product or composition that is intended for consumption by a companion animal, such as a cat, a dog, a guinea pig, a rabbit, a bird or a horse. For example, but not by way of limitation, the companion animal can be a "domestic" dog, e.g., *Canis lupus familiaris*. In certain embodiments, the companion animal can be a "domestic" cat such as *Felis domesticus*. A "pet food" or "pet food composition" or "pet food product" or "final pet food product" includes any food, feed, snack, food supplement, liquid, beverage, treat, toy (chewable and/or consumable toys), meal substitute or meal replacement.

As used herein, the term "predetermined reference value" or "reference value" refers to a threshold level of a biomarker by comparing with which, a diagnosis of CKD can be made. The reference value can be a threshold value or a reference range. In certain embodiments, a reference value can be derived from ROC curve analysis, selecting the reference value as that which maximizes sensitivity while keeping the specificity above a user-defined threshold. In certain embodiments, the reference value can be selected as that which maximizes specificity while keeping the sensitivity above a user-defined threshold, for example, 80% sensitivity. In certain embodiments, a reference value can be the upper limit of the range of a biomarker levels produced from a population of healthy subjects, if the biomarker is increased in subjects having CKD, i.e., the predetermined algorithm is positive logic. Conversely, a reference value can be the lower limit of the range of a biomarker levels or produced from a population of healthy subjects, if the biomarker is decreased in subjects having CKD, i.e., the algorithm is negative logic.

The term "control population" means a control group of animals which do not have chronic kidney disease, and which have not had any variables manipulated. The selection of the animals to be included in the control groups may be based on genetic background, average health status, age, history of nutrition, vaccination or prophylactic treatment. In certain embodiments, a control population can be a group of at least 3, preferably at least 10, more preferred at least 50 animals with a similar genetic background, age and average health status.

2. Biomarkers

In certain non-limiting embodiments, the presently disclosed subject matter provides for biomarkers and methods of using the same to diagnose an animal as being at risk for chronic kidney disease (CKD) and/or determine the progression of CKD.

The term "biomarker" as used herein, refers to any biological compound related to the progressive development of a disease of interest. In particular, a biomarker for diagnosing CKD is any biological compound related to the progression of CKD. The treatment of kidney disease may be tailored depending upon the progression of CKD indicated by the biomarkers related to the progression of CKD, and the prediction of recovery can be determined by monitoring the biomarkers.

In certain embodiments, the biomarker is magnesium. In certain embodiments, the biomarker is the total magnesium in the blood of the animal. In certain embodiments, the biomarker is the magnesium in the serum of the animal. In certain embodiments, the biomarker is the magnesium in the plasma of the animal. In certain embodiments, the biomarker is the magnesium in a urine sample of the animal.

In certain embodiments, a change in magnesium level is associated with CKD. In certain embodiments, an increased magnesium level indicates the progression of CKD and/or an increased risk of developing CKD. In certain embodiments, a decreased magnesium level indicates the progression of CKD and/or an increased risk of developing CKD. In certain embodiments, a higher magnesium level compared to a predetermined reference values based on average magnesium levels in blood in a control population indicates the progression of CKD and/or an increased risk of developing CKD. In certain embodiments, a lower magnesium level compared to a predetermined reference values based on average magnesium levels in blood in a control population indicates the progression of CKD and/or an increased risk of developing CKD.

In certain embodiments, a change in magnesium level is associated with mortality rate and/or survival rate. In certain embodiments, an increased magnesium level indicates an increased mortality rate and/or a decreased survival rate. In certain embodiments, a decreased magnesium level indicates an increased mortality rate and/or a decreased survival rate. In certain embodiments, a higher magnesium level compared to a predetermined reference values based on average magnesium levels in blood in a control population indicates a higher mortality rate and/or a lower survival rate. In certain embodiments, a lower magnesium level compared to a predetermined reference values based on average magnesium levels in blood in a control population indicates a higher mortality rate and/or a lower survival rate.

In certain embodiments, a change in magnesium level is associated with increased mortality rate of a hyperphosphatemic animal. In certain embodiments, an increased magnesium level indicates an increased mortality rate of a hyperphosphatemic animal. In certain embodiments, a decreased magnesium level indicates an increased mortality rate of a hyperphosphatemic animal. In certain embodiments, a higher magnesium level compared to a predetermined reference values based on average magnesium levels in blood in a control population indicates a higher mortality rate of a hyperphosphatemic animal. In certain embodiments, a lower magnesium level compared to a predetermined reference values based on average magnesium levels in blood in a control population indicates a higher mortality rate of a hyperphosphatemic animal.

In certain embodiments, the method of diagnosing and treating an animal at risk for chronic kidney disease (CKD) comprises: obtaining a blood sample from the animal; determining an amount of magnesium in the blood sample of the animal; comparing the amount of magnesium to predetermined reference values; wherein the predetermined reference values are based on average magnesium levels in blood in a control population; diagnosing the animal as being at risk for the CKD if the amount of magnesium is below a first predetermined value or above a second predetermined reference value; and providing the animal with a treatment regimen if the amount of magnesium is below a first predetermined value or above a second predetermined reference value.

In certain embodiments, the biomarker further comprises fibroblast growth factor 23 (FGF23). In certain embodiments, the biomarker is the total FGF23 in the blood of the animal. In certain embodiments, the biomarker is the FGF23 in the serum of the animal. In certain embodiments, the biomarker is the FGF23 in the plasma of the animal. In certain embodiments, the biomarker is the FGF23 in a urine sample of the animal.

In certain embodiments, a magnesium level is inversely associated with FGF23 levels in an animal. In certain embodiments, a decreased magnesium level indicates an increased FGF23 level in an animal. In certain embodiments, an increased magnesium level indicates a decreased FGF23 level in an animal.

In certain embodiments, the method of diagnosing and treating an animal at risk for chronic kidney disease (CKD) further comprises the steps of determining an amount of FGF23 in the blood sample of the animal; comparing the amount of FGF23 to a third predetermined reference value; and wherein the predetermined reference value is based on an average FGF23 level in blood in a control population, and wherein a higher FGF23 level compared to the second predetermined reference value indicates a higher likelihood of effective treatment.

In certain embodiments, the biomarker comprises at least one further biomarker. In certain embodiments, the at least one further biomarker is selected from the renal biomarkers disclosed in U.S. Publication No. 2012/0077690 A1, U.S. Publication No. 2013/0323751 A1, EP 3,112,871 A1, EP 2,462,445 A1, and EP 3,054,301 A1. In certain embodiments, the at least one further biomarker is selected from the group consisting of phosphate, creatinine, blood urine nitrogen (BUN) and parathyroid hormone (PTH), In certain embodiments, the at least one further biomarker is selected from the group consisting of phosphate, creatinine, blood urine nitrogen (BUN), parathyroid hormone (PTH), symmetric dimethylarginine (SDMA), systolic blood pressure, potassium, total calcium, hyaluronic acid, death receptor 5, transforming growth factor (31, ferritin, beta globin, catalase, alpha globin, epidermal growth factor receptor pathway substrate 8, mucin isoform precursor, ezrin, delta globin, moesin, phosphoprotein isoform, annexin A2, myoglobin, hemopexin, serine proteinase inhibitor, serpine peptidase inhibitor, CD14 antigen precursor, fibronectin isoform preprotein, angiotensinogen preprotein, complement component precursor, carbonic anhydrase, uromodulin precursor, complement factor H, complement component 4 BP, heparan sulfate proteoglycan 2, olfactomedian-4, leucine rich alpha-2 glycoprotein, ring finger protein 167, inter-alpha globulin inhibitor H4, heparan sulfate proteoglycan 2, N-acylshingosine aminohydrolase, serine proteinase inhibitor clade A member 1, mucin 1, clusterin isoform 1, brain abundant membrane attached signal protein 1, dipeptidase 1, fibronectin 1 isoform 5 preprotein, angiotensinogen preprotien, carbonic anhydrase, uromodulin precursor, Metalloproteinase inhibitor 2, Insulin-like growth factor-binding protein 7, Immunoglobulin A, Immunoglobulin G1, Immunoglobulin G2, Alpha-1 antitrypsin, Serum amyloid P component, Hepatocyte growth factor, Intercellular adhesion molecule 1, Beta-2-glycoprotein 1, Interleukin-1 beta, Neutrophil Elastase, Tumor necrosis factor receptor superfamily member 11B, Interleukin-11, Cathepsin D, C-C motif chemokine 24, C-X-C motif chemokine 6, C-C motif chemokine 13, C-X-C motif chemokines-1, -2, and -3, Matrilysin, Interleukin-2 receptor alpha chain, Insulin-like growth factor-binding protein 3, Macrophage colony-stimulating factor 1, apolipoprotein C-I, apolipoprotein C-II, fibrinogen alpha chain, fibrinogen A-alpha chain, kininogen, Inter-Alpha Inhibitor H4 (ITIH4), keratin Type I cytoskeletol 10 cystatin A, cystatin B and combinations thereof.

In certain embodiments, magnesium level is inversely associated with blood pressure in an animal. In certain embodiments, a decreased magnesium level indicates an increased blood pressure, hypertension and/or an increased risk of developing hypertension in an animal. In certain embodiments, an increased magnesium level indicates a decreased blood pressure in an animal. In certain embodiments, low magnesium level compared to an average level in a group of an animal indicates hypertension or an increased risk of developing hypertension in an animal. In certain embodiments, the blood pressure is selected from the group consisting of systolic pressure, diastolic pressure, systemic arterial pressure, mean arterial pressure, pulse pressure, systemic venous pressure pulmonary pressure, and combinations thereof. In certain embodiments, the blood pressure is measured as a systolic pressure. In certain embodiments, the blood pressure is measured as a diastolic pressure.

In certain embodiments, the at least one further biomarker is in the blood of the animal. In certain embodiments, the at least one further biomarker is in the serum of the animal. In certain embodiments, the at least one further biomarker is in the plasma of the animal. In certain embodiments, the at least one further biomarker is in a urine sample of the animal.

In certain embodiments, the method of diagnosing and treating an animal at risk for chronic kidney disease (CKD) further comprises determining an amount of at least one further biomarker in the blood sample, and comparing the amount of the at least one further biomarker to a fourth predetermined reference value. In certain embodiments, the amount of the at least one further biomarker being above the fourth predetermined reference value indicates a higher likelihood of effective treatment. In certain embodiments, the amount of the at least one further biomarker being below the fourth predetermined reference value indicates a higher likelihood of effective treatment.

In certain embodiments, the predetermined reference value of a biomarker can be based on an average amount of the biomarker in the tested blood in a control population. The control population can be a group of at least 3, preferably at least 10, more preferred at least 50 animals with a similar genetic background, age and average health status.

In certain embodiments, the first predetermined reference value of magnesium in the blood sample is less than about 90%, 80%, 70%, 60%, 50%, 40%, 30%, 20%, 10%, 5%, 2%, or 1%, of the average amount of magnesium in blood in a control population. In certain embodiments, the first predetermined reference value of magnesium in the blood sample is less than about 50% of the average amount of magnesium in blood in a control population. In certain embodiments, the second predetermined reference value of magnesium in the blood sample is more than about 110%, 120%, 130%, 140%, 150%, 160%, 170%, 180%, 190%, 200%, 250%, 300%, 400%, 500%, 600%, 700%, 800%, 900%, or 1000% of the average amount of magnesium in blood in a control population. In certain embodiments, the second predetermined reference value of magnesium in the blood sample is more than about 120% of the average amount of magnesium in blood in a control population.

In certain embodiments, the third predetermined reference value of FGF23 in the blood sample is more than about 110%, 120%, 130%, 140%, 150%, 160%, 170%, 180%, 190%, 200%, 250%, 300%, 400%, 500%, 600%, 700%, 800%, 900%, or 1000% of the average amount of FGF23 in blood in a control population. In certain embodiments, the second predetermined reference value of FGF23 in the blood sample is more than about 150% of the average amount of FGF23 in blood in a control population In certain embodiments, the amounts of the biomarkers in the animal can be detected and quantified by any means known in the art. In certain embodiments, the amount of magnesium is determined by mass spectroscopy, e.g., UPLC-ESI-MS/MS or inductively coupled plasma mass spectrometry (ICP-MS), a fluorescence method or a luminescence method. In certain embodiments, Magnesium Green, Mag-Fura-2 and/or Mag-Indo-1 are used to determine the amount of magnesium.

In certain embodiments, the amount of FGF23 is determined by an antibody-based detection method. In certain embodiments, a FGF23 antibody is used to determine the amount of FGF23. In certain embodiments, the amount of FGF23 is determined by an enzyme-linked immunosorbent assay (ELISA). In certain embodiments, the amount of FGF23 is determined by a sandwich ELISA.

In certain embodiments, other detection methods, such as other spectroscopic methods, chromatographic methods, labeling techniques, or quantitative chemical methods can be used. In certain embodiments, the amount of the biomarkers in the animal and the reference values are determined by the same method.

3. Treatment Methods

In certain non-limiting embodiments, the presently disclosed subject matter provides for methods of treating or delaying progression of chronic kidney disease (CKD) in an animal in need thereof. In certain embodiments, the method comprises providing the animal with a composition comprising magnesium or salt thereof to treat the animal.

The compositions and methods of the presently disclosed subject matter can be useful for a variety of mammals, including non-human mammals such as non-human primates (e.g., monkeys, chimpanzees, etc.), pets/companion animals (e.g., dogs, cats, equine, etc.), farm animals (e.g., goats, sheep, swine, bovine, etc.), laboratory animals (e.g., mice, rats, etc.), and wild and zoo animals (e.g., wolves, bears, deer, etc.).

In certain non-limiting embodiments of the presently disclosed subject matter, for example, the animal is a monogastric mammal (i.e., a mammal having a single stomach), such as, for example, a non-human primate, dog, cat, rabbit, horse, or swine.

In certain non-limiting embodiments of the presently disclosed subject matter, the animal is a carnivorous mammal, i.e., a meat-eating mammal.

In other embodiments of the presently disclosed subject matter, the animal is an omnivorous mammal, i.e., a mammal that eats both plants and meat.

In certain non-limiting embodiments, the subject is a cat or a dog.

In certain non-limiting embodiments, the subject is at risk of chronic kidney disease.

In certain non-limiting embodiments, the subject is not known to be at risk of chronic kidney disease.

In certain non-limiting embodiments, the subject suffers from chronic kidney disease.

In certain non-limiting embodiments, the subject is not known to suffer from chronic kidney disease.

In certain non-limiting embodiments, the subject is under a treatment for chronic kidney disease. In certain non-limiting embodiments, the treatment is a dietary therapy.

In certain non-limiting embodiments, the presently disclosed subject matter provides for methods of treating or delaying the progression of chronic kidney disease (CKD) in an animal, wherein the method comprises: determining an amount of magnesium in a blood sample of the animal; comparing the amount of magnesium to a predetermined reference value; wherein the predetermined reference value is based on an average magnesium level in blood in a control population; and providing the animal with a composition comprising magnesium or salt thereof to treat the animal if the amount of magnesium is below the predetermined reference value.

In certain non-limiting embodiments, the presently disclosed subject matter provides for methods of treating or delaying progression of chronic kidney disease (CKD) in an animal in need thereof, wherein the animal has a magnesium deficiency compared to a predetermined reference value, the method comprising: administering a composition comprising an effective amount of magnesium or salt thereof, and wherein the predetermined reference value is based on an average magnesium level in blood in a control population.

In certain non-limiting embodiments, the presently disclosed subject matter provides for methods of treating or delaying progression of chronic kidney disease (CKD) in an animal in need thereof, wherein the method comprises: determining an amount of magnesium in a blood sample of the animal; comparing the amount of magnesium to predetermined reference values; wherein the predetermined reference values are based on average magnesium levels in blood in a control population; and providing the animal with a treatment regimen if the amount of magnesium is below a first predetermined value or above a second predetermined reference value.

In certain non-limiting embodiments, the presently disclosed subject matter provides for methods of diagnosing and treating an animal at risk for chronic kidney disease (CKD), wherein the method comprises: obtaining a blood sample from the animal; determining an amount of magnesium in the blood sample of the animal; comparing the amount of magnesium to predetermined reference values; wherein the predetermined reference values are based on average magnesium levels in blood in a control population; diagnosing the animal as being at risk for the CKD if the amount of magnesium is below a first predetermined value or above a second predetermined reference value; and providing the animal with a treatment regimen if the amount of magnesium is below a first predetermined value or above a second predetermined reference value.

In certain embodiments, the method further comprising the steps of determining an amount of FGF23 in the blood sample of the animal; comparing the amount of FGF23 to a third predetermined reference value; and wherein the predetermined reference value is based on an average FGF23 level in blood in a control population, and wherein a higher FGF23 level compared to the second predetermined reference value indicates a higher likelihood of effective treatment.

In certain embodiments, the method of diagnosing and treating an animal at risk for chronic kidney disease (CKD) further comprises determining an amount of at least one further biomarker in the blood sample, and comparing the amount of the at least one further biomarker to a fourth predetermined reference value. In certain embodiments, the amount of the at least one further biomarker being above the fourth predetermined reference value indicates a higher likelihood of effective treatment. In certain embodiments, the amount of the at least one further biomarker being below the fourth predetermined reference value indicates a higher likelihood of effective treatment.

In certain embodiments, method of any one of the preceding claims, further comprising: determining an amount of at least one further biomarker selected from the group consisting of phosphate, creatinine, blood urine nitrogen (BUN) and parathyroid hormone (PTH) in the blood sample, and comparing the amount of the at least one further biomarker to a fourth predetermined reference value, wherein the amount of phosphate, creatinine, blood urine nitrogen (BUN) and/or parathyroid hormone (PTH) being above the fourth predetermined reference value indicates a higher likelihood of effective treatment.

In certain embodiments, the fourth predetermined reference value of the one further biomarker is more than about 110% or more of the average value of the one further biomarker in a control population (meaning 10% over the average value). In other embodiments, the fourth predetermined reference value of the one further biomarker is more than about 120%, 130%, 140%, 150%, 160%, 170%, 180%, 190%, 200%, 250%, 300%, 400%, 500%, 600%, 700%, 800%, 900%, 1000% or more of the average value of the one further biomarker in a control population.

In certain embodiments, the method further comprises maintaining the animal on the composition for a sufficient period of time to reduce the amount of FGF23 in the animal.

In certain embodiments, the methods provided in the presently disclosed subject matter further comprises: determining blood pressure of the animal, comparing the blood pressure to a fifth predetermined reference value, and administrating a prevention or treatment regimen of hypertension if the blood pressure is higher than the fifth predetermined reference value. In certain embodiments, the blood pressure is selected from the group consisting of systolic pressure, diastolic pressure, systemic arterial pressure, mean arterial pressure, pulse pressure, systemic venous pressure pulmonary pressure, and combinations thereof. In certain embodiments, the blood pressure is a systolic pressure. In certain embodiments, the blood pressure is a diastolic pressure.

In certain embodiments, the fifth predetermined reference value of blood pressure is more than about 110%, 120%, 130%, 140%, 150%, 160%, 170%, 180%, 190%, 200% or more of the average blood pressure in a control population. In certain embodiments, the fifth predetermined reference value is more than about 120% of the average blood pressure in a control population.

In certain embodiments, the treatment regimen comprises at least one treatment regimen selected from the group consisting of a dietary therapy, hemodialysis, renal replacement therapy, withdrawal of kidney damaging compounds, kidney transplantation, delaying or avoiding kidney damaging procedures, modifying diuretic administration, and combinations thereof. In certain embodiments, the treatment regimen comprises at least one treatment regimen selected from the group consisting of administering a composition comprising an effective amount of magnesium or a salt thereof, reducing phosphate intake, reducing protein intake, administering polyunsaturated fatty acids, administering a phosphate binder therapy, administering potassium, reducing dietary sodium intake, administering alkali supplements, and combinations thereof. In certain embodiments, the treatment regimen comprises any treatment methods described in Jonathan D. Forster, Update on Mineral and Bone Disorders in Chronic Kidney Disease. Vet Clin North Am Small Anim Pract. 2016 November; 46(6):1131-49, the content of which is hereby incorporated by reference in its entirety.

In certain embodiments, the treatment regimen is a dietary therapy. In certain embodiments, the dietary therapy comprises a diet selected from the group consisting of a high magnesium diet, a low phosphorous diet, a low protein diet, a low sodium diet, a high potassium diet, a polyunsaturated fatty acids (PUFA) diet, and combinations thereof. In certain embodiments, the dietary therapy is any one of the dietary therapies described in Elliott et al., Dietary therapy for feline chronic kidney disease, Encyclopedia of feline clinical nutrition, 2nd edition, 2015, the content of which is hereby incorporated by reference in its entirety.

In certain embodiments, the composition is a pet food product. In certain embodiments, the amount of the magnesium is between about 200 mg/1000 Kcal and about 500 mg/1000 Kcal.

In certain embodiments, the composition is a dietary supplement. In certain embodiments, the amount of the magnesium added to a pet food product is between about 50 mg/1000 Kcal and about 200 mg/1000 Kcal.

In certain embodiments, the magnesium in the composition is at an amount of about 10 mg/kcal to about 1000 mg/kcal. For example, and not by way of limitation, the magnesium can be at an amount of about 10 mg/kcal to about 100 mg/kcal, about 20 mg/kcal to about 100 mg/kcal, about 10 mg/kcal to about 200 mg/kcal, about 20 mg/kcal to about 200 mg/kcal, about 50 mg/kcal to about 100 mg/kcal, about 50 mg/kcal to about 200 mg/kcal, about 50 mg/kcal to about 300 mg/kcal, about 100 mg/kcal to about 200 mg/kcal, about 100 mg/kcal to about 300 mg/kcal, about 100 mg/kcal to about 400 mg/kcal, about 100 mg/kcal to about 500 mg/kcal, about 200 mg/kcal to about 500 mg/kcal, about 300 mg/kcal to about 500 mg/kcal, about 200 mg/kcal to about 600 mg/kcal, about 200 mg/kcal to about 700 mg/kcal, about 200 mg/kcal to about 800 mg/kcal, about 300 mg/kcal to about 600 mg/kcal, about 300 mg/kcal to about 700 mg/kcal, about 300 mg/kcal to about 800 mg/kcal, about 400 mg/kcal to about 600 mg/kcal, about 400 mg/kcal to about 700 mg/kcal, about 400 mg/kcal to about 800 mg/kcal or about 500 mg/kcal to about 800 mg/kcal. In certain embodiments, the magnesium in the composition is at an amount of about 200 mg/kcal to about 500 mg/kcal, e.g., about 300 mg/kcal. In certain embodiments, the magnesium in the composition is at an amount of about 50 mg/kcal to about 200 mg/kcal, e.g., about 100 mg/kcal.

Magnesium used in compositions and methods of this presently disclosed subject matter can be in a form of a magnesium salt or a magnesium coordination complex.

In certain embodiments, the magnesium is a magnesium salt for example, but not limited to, an acetate salt, a TFA salt, or a formate salt. In certain embodiments, the magnesium salt comprises an anion (−) (for example, but not limited to, an amino acid anion, $Cl^-$, $F^-$, $Br^-$, $O^{2-}$, $CO_3^{2-}$, $HCO_3^-$, $OH^-$, $NO_3^-$, $PO_4^{3-}$, $SO_4^{2-}$, $CH_3COO^-$, $HCOO^-$, $C_2O_4^{2-}$ and $CN^-$) bonded via an ionic bond with $Mg^{2+}$.

In certain embodiments, the magnesium is in a form of an inorganic magnesium salt. In certain embodiments, the magnesium is magnesium oxide. In certain embodiments, the magnesium oxide is in an amount of no more than 0.25% weight by weight of the composition (e.g., a pet food or a dietary supplement) provided to the animal. In certain embodiments, the magnesium oxide is in an amount of no more than 0.22% weight by weight of the composition. In certain embodiments, the magnesium oxide is in an amount of no more than 0.2% weight by weight of the composition. In certain embodiments, the magnesium is in a form of an organic magnesium salt.

In certain embodiments, the magnesium compound is a magnesium coordination complex. In certain embodiments, the magnesium coordination complex is a chlorophyll. In certain embodiments, the magnesium compound is chlorophyll a, chlorophyll b, chlorophyll c1, chlorophyll c2, chlorophyll d, chlorophyll for combination thereof.

In certain embodiments, the magnesium can be fed to an animal thrice every day, twice every day, once every day, once every two days, once every three days, once every four days, once every five days, once every six days, once a week, once every two weeks, once every three weeks, or once every month. In certain embodiments, the magnesium can be fed to an animal one or more times per day. For example, and not by way of limitation, the magnesium can be administered once, twice, three, four, five or more times a day. In certain embodiments, the magnesium can be fed to an animal in a constant manner, e.g., where the animal grazes on a constantly available supply of a pet food composition comprising magnesium.

4. End Products

In certain non-limiting embodiments, the presently disclosed subject matter provides products suitable for treating or delaying the progression of chronic kidney disease (CKD). In certain embodiments, the product is a pet food composition. In certain embodiments, the pet food composition contains an effective amount of magnesium. In certain embodiments, the magnesium in the pet food composition can be in a form of a magnesium salt or a magnesium coordination complex. In certain embodiments, the magnesium is in any of the forms described in Section 3 of the detailed description.

In certain embodiments, magnesium in the pet food composition is at an amount of about 10 mg/kcal to about 1000 mg/kcal. For example, and not by way of limitation, magnesium can be at an amount of about 10 mg/kcal to about 100 mg/kcal, about 20 mg/kcal to about 100 mg/kcal, about 10 mg/kcal to about 200 mg/kcal, about 20 mg/kcal to about 200 mg/kcal, about 50 mg/kcal to about 100 mg/kcal, about 50 mg/kcal to about 200 mg/kcal, about 50 mg/kcal to about 300 mg/kcal, about 100 mg/kcal to about 200 mg/kcal, about 100 mg/kcal to about 300 mg/kcal, about 100 mg/kcal to about 400 mg/kcal, about 100 mg/kcal to about 500 mg/kcal, about 200 mg/kcal to about 500 mg/kcal, about 300 mg/kcal to about 500 mg/kcal, about 200 mg/kcal to about 600 mg/kcal, about 200 mg/kcal to about 700 mg/kcal, about 200 mg/kcal to about 800 mg/kcal, about 300 mg/kcal to about 600 mg/kcal, about 300 mg/kcal to about 700 mg/kcal, about 300 mg/kcal to about 800 mg/kcal, about 400 mg/kcal to about 600 mg/kcal, about 400 mg/kcal to about 700 mg/kcal, about 400 mg/kcal to about 800 mg/kcal or about 500 mg/kcal to about 800 mg/kcal. In certain embodiments, magnesium in the pet food composition is at an amount of about 200 mg/kcal to about 500 mg/kcal, e.g., about 300 mg/kcal. In certain embodiments, magnesium in the pet food composition is at an amount of about 50 mg/kcal to about 200 mg/kcal, e.g., about 100 mg/kcal.

In certain embodiments, magnesium in the pet food composition is at an amount of about 10 mg to about 1000 mg per daily serving or unit dosage. For example, and not by way of limitation, magnesium can be at an amount of about 10 mg to about 500 mg per daily serving or unit dosage, about 10 mg to about 400 mg per daily serving or unit dosage, about 10 mg to about 300 mg per daily serving or unit dosage, about 10 mg to about 200 mg per daily serving or unit dosage, about 20 mg to about 200 mg per daily serving or unit dosage, about 30 mg to about 200 mg per daily serving or unit dosage, about 40 mg to about 200 mg per daily serving or unit dosage, about 50 mg to about 200 mg per daily serving or unit dosage, about 50 mg to about 150 mg per daily serving or unit dosage, about 50 mg to about 140 mg per daily serving or unit dosage, about 50 mg to about 130 mg per daily serving or unit dosage, about 50 mg to about 120 mg per daily serving or unit dosage, about 500 mg to about 110 mg per daily serving or unit dosage, about 50 mg to about 100 mg per daily serving or unit dosage, about 10 mg to about 50 mg per daily serving or unit dosage, about 100 mg to about 150 mg per daily serving or unit dosage, about 150 mg to about 200 mg per daily serving or unit dosage, about 100 mg to about 200 mg per daily serving or unit dosage, about 100 mg to about 300 mg per daily serving or unit dosage, about 100 mg to about 400 mg per daily serving or unit dosage, about 100 mg to about 500 mg per daily serving or unit dosage, about 200 mg to about 500 mg per daily serving or unit dosage, about 300 mg to about 500 mg per daily serving or unit dosage, about 200 mg to about 800 mg per daily serving or unit dosage or about 500 mg to about 1000 mg per daily serving or unit dosage. In certain embodiments, magnesium in the pet food composition is at an amount of about 20 mg to about 200 mg per daily serving or unit dosage, e.g., about 100 mg per daily serving or unit dosage. In certain embodiments, magnesium in the pet food composition is at an amount of about 50 mg to about 100 mg per daily serving or unit dosage, e.g., about 75 mg per daily serving or unit dosage. In certain embodiments, magnesium in the pet food composition is at an amount of about 60 mg to about 90 mg per daily serving or unit dosage.

In certain embodiments, magnesium in the pet food composition is at an amount of about 0.001% to about 10% weight by weight of the pet food composition. For example, and not by way of limitation, magnesium can be at an amount of about 0.001% to about 0.01% weight by weight, about 0.01% to about 0.1% weight by weight, about 0.1% to about 1% weight by weight, about 1% to about 10% weight by weight, about 0.01% to about 0.5% weight by weight, about 0.01% to about 0.25% weight by weight, about 0.01% to about 0.2% weight by weight, about 0.01% to about 0.15% weight by weight, about 0.01% to about 0.1% weight by weight, about 0.01% to about 0.05% weight by weight, about 0.1% to about 0.15% weight by weight, about 0.1% to about 0.2% weight by weight, about 0.1% to about 0.25% weight by weight, about 0.1% to about 0.5% weight by weight, about 0.5% to about 1% weight by weight, about 0.1% to about 2% weight by weight, about 0.1% to about 5% weight by weight, about 0.1% to about 10% weight by weight, about 2% to about 10% weight by weight, and about 5% to about 10% weight by weight. In certain embodiments, magnesium in the pet food composition is at an amount of no more than about 0.25% weight by weight. In certain embodiments, magnesium in the pet food composition is at an amount of no more than about 0.2% weight by weight. In certain embodiments, magnesium in the pet food composition is at an amount of no more than about 0.15% weight by weight. In certain embodiments, magnesium in the pet food composition is at an amount of no more than about 0.1% weight by weight. In certain embodiments, magnesium in the pet food composition is at an amount of no more than about 0.05% weight by weight.

In certain embodiments, the pet food composition of the presently disclosed subject matter can be fed to an animal thrice every day, twice every day, once every day, once every two days, once every three days, once every four days, once every five days, once every six days, once a week, once every two weeks, once every three weeks, or once every month. In certain embodiments, the pet food composition can be fed to an animal one or more times per day. For example, and not by way of limitation, the pet food composition can be administered once, twice, three, four, five or more times a day. In certain embodiments, the pet food composition can be fed to an animal in a constant manner, e.g., where the animal grazes on a constantly available supply of the pet food composition.

In certain embodiments, a formulation of the presently disclosed subject matter can further comprise an additional active agent. Non-limiting examples of additional active agents that can be present within a formulation of the presently disclosed subject matter include a nutritional agent (e.g., amino acids, proteins, fatty acids, carbohydrates, sugars, nucleic acids, nucleotides, vitamins, minerals, etc.), an anti-angiogenic agent, a steroid, an mTOR inhibitor (e.g., everolimus), a beta-blocker (e.g., propranolol), and/or an agent that reduces blood pressure.

In certain embodiments, the pet food composition can further contain additives known in the art. In certain embodiments, such additives are present in amounts that do not impair the purpose and effect provided by the presently disclosed subject matter. Examples of contemplated additives include, but are not limited to, substances that are functionally beneficial to improving kidney function, substances with a stabilizing effect, organoleptic substances, processing aids, substances that enhance palatability, coloring substances, and substances that provide nutritional benefits. In certain embodiments, the stabilizing substances include, but are not limited to, substances that tend to increase the shelf life of the composition. In certain embodiments, such substances include, but are not limited to, preservatives, synergists and sequestrants, packaging gases, stabilizers, emulsifiers, thickeners, gelling agents, and humectants. In certain embodiments, the emulsifiers and/or thickening agents include, for example, gelatin, cellulose ethers, starch, starch esters, starch ethers, and modified starches.

In certain embodiments, the additives for coloring, palatability, and nutritional purposes include, for example, colorants; iron oxide, sodium chloride, potassium citrate, potassium chloride, and other edible salts; vitamins; minerals; and flavoring. The amount of such additives in a composition typically is up to about 5% (dry basis of the composition).

In certain embodiments, the pet food composition is a dietary supplement. In certain embodiments, the dietary supplements include, for example, a feed used with another feed to improve the nutritive balance or performance of the total. In certain embodiments, the supplements include compositions that are fed undiluted as a supplement to other feeds, offered free choice with other parts of an animal's ration that are separately available, or diluted and mixed with an animal's regular feed to produce a complete feed. The AAFCO, for example, provides a discussion relating to supplements in the American Feed Control Officials, Incorp. Official Publication, p. 220 (2003). Supplements can be in various forms including, for example, powders, liquids, syrups, pills, encapsulated compositions, etc.

In certain embodiments, the pet food composition is a treat. In certain embodiments, treats include, for example, compositions that are given to an animal to entice the animal to eat during a non-meal time. In certain embodiments, the pet food composition is a treat for canines include, for example, dog bones. Treats can be nutritional, wherein the composition comprises one or more nutrients, and can, for example, have a composition as described above for food. Non-nutritional treats encompass any other treats that are non-toxic.

In certain embodiments, the magnesium of the presently disclosed subject matter can be incorporated into the composition during the processing of the formulation, such as during and/or after mixing of other components of the composition. Distribution of these components into the composition can be accomplished by conventional means.

In certain embodiments, pet food compositions of the presently disclosed subject matter can be prepared in a canned or wet form using conventional pet food processes. In certain embodiments, ground animal (e.g., mammal, poultry, and/or fish) proteinaceous tissues are mixed with the other ingredients, including fish oils, cereal grains, other nutritionally balancing ingredients, special purpose additives (e.g., vitamin and mineral mixtures, inorganic salts, cellulose and beet pulp, bulking agents, and the like); and water that sufficient for processing is also added. These ingredients are mixed in a vessel suitable for heating while blending the components. Heating of the mixture can be effected using any suitable manner, such as, for example, by direct steam injection or by using a vessel fitted with a heat exchanger. Following the addition of the last ingredient, the mixture is heated to a temperature range of from about 50° F. to about 212° F. Temperatures outside this range are acceptable but can be commercially impractical without use of other processing aids. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. This is usually accomplished by heating to temperatures of greater than about 230° F. for an appropriate time, which is dependent on, for example, the temperature used and the composition.

In certain embodiments, pet food compositions of the presently disclosed subject matter can be prepared in a dry form using conventional processes. In certain embodiments, dry ingredients, including, for example, animal protein sources, plant protein sources, grains, etc., are ground and mixed together. In certain embodiments, moist or liquid ingredients, including fats, oils, animal protein sources, water, etc., are then added to and mixed with the dry mix. In certain embodiments, the mixture is then processed into kibbles or similar dry pieces. In certain embodiments, the pet food composition is kibble. In certain embodiments, kibble is formed using an extrusion process in which the mixture of dry and wet ingredients is subjected to mechanical work at a high pressure and temperature and forced through small openings and cut off into kibble by a rotating knife. In certain embodiments, the wet kibble is then dried and optionally coated with one or more topical coatings which can include, for example, flavors, fats, oils, powders, and the like. In certain embodiments, kibble can also be made from the dough using a baking process, rather than extrusion, wherein the dough is placed into a mold before dry-heat processing.

In certain embodiments, treats of the presently disclosed subject matter can be prepared by, for example, an extrusion or baking process similar to those described above for dry food.

EXAMPLES

The presently disclosed subject matter will be better understood by reference to the following Example, which is provided as exemplary of the invention, and not by way of limitation.

A listing of abbreviations used are set forth below:
CKD chronic kidney disease
CKD-MBD chronic kidney disease-mineral and bone disorder
FE fractional excretion
FGF-23 fibroblast growth factor 23
$HCO_3^-$ venous bicarbonate concentration
HR hazard ratio
IRIS International Renal Interest Society
OR odds ratio
PTH parathyroid hormone
SBP systolic blood pressure
USG urine specific gravity

Example 1: Total Magnesium is a Predictor of Survival Time in Cats with Chronic Kidney Disease Hypomagnesemia is associated with decreased survival times in humans with chronic kidney disease (CKD). Little is known about the prognostic value of magnesium in feline CKD. This study aimed to evaluate if plasma total magnesium concentration at diagnosis of CKD was associated with survival times in cats. The effect of fibroblast growth factor 23 (FGF23) concentration was also explored, given recent evidence suggesting it to be an important prognostic factor in feline CKD.

Total magnesium concentrations (tMg) were measured on stored heparinized plasma samples obtained from cats at diagnosis of azotemic CKD. Clinical data were presented as median [25th, 75th percentile]. Cats were categorized into quartiles (MgQ1-4) based on tMg, and comparisons of baseline variables between groups were made with a one-way ANOVA. Two multivariable Cox regression models were used to assess the utility of plasma tMg at diagnosis of azotemic CKD as a predictor of survival time (all-cause mortality): model 1, including age, plasma creatinine, phosphate, intact parathyroid hormone, albumin, tMg, and a diagnosis of hypertension as categorical variables, and packed cell volume (PCV) as a continuous variable, and model 2, including FGF23 as a categorical variable in addition to those included in model 1.

One hundred and sixty (160) cats in IRIS stage 2 (n=110) and 3 (n=50) CKD were included in this retrospective observational cohort study. The median tMg in the study was 2.04 [1.85, 2.24] mg/dL, range: 1.29-2.90 mg/dL. Cats in MgQ1 had a significantly higher FGF23 concentration (2008.7 [762.1, 8194.4] pg/mL) compared to all three upper quarters, which did not significantly differ from each other (MgQ2: 895.3 [455.0, 1948.2]; MgQ3: 493.9 [344.2, 2035.5]; MgQ4: 477.8 [316.9, 975.7] pg/mL, P<0.001). Cats in MgQ1 and MgQ3 differed in age (Q1:16.4 [14.1, 18.7]; Q3:13.4 [12.0, 15.9] years, P=0.022) and in phosphate concentration (Q1:5.15 [3.89, 6.54]; Q3:4.09 [3.50, 5.05] mg/dL, P=0.013). Creatinine concentration differed between MgQ3 and MgQ4 only (MgQ3:2.37 [2.14, 2.68]; MgQ4: 2.68 [2.38, 3.30] mg/dL, P=0.029). In Cox regression model 1, survival was positively associated with PCV (P<0.001) and negatively associated with age (P<0.001), creatinine (P=0.003), tMg (P=0.007), and a diagnosis of hypertension (P=0.046). Cats in MgQ2 had reduced risk of death compared to both MgQ1 (hazard ratio (HR):0.434, P=0.003) and MgQ4 (HR: 0.433, P=0.002). In model 2, survival was positively associated with PCV (P<0.001) and negatively associated with age (P<0.001), FGF23 (P=0.004), hypertension (P=0.014), and tMg (P=0.036). Cats in MgQ2 had a significantly reduced mortality risk compared to MgQ4 (HR: 0.452, P=0.005), but no longer compared to MgQ1 (HR: 0.622, P=0.126).

In conclusion, higher plasma magnesium concentration at diagnosis of CKD was associated with an increased risk of all-cause mortality after accounting for the effect of FGF23. Intermediate magnesium concentrations improved survival. Cats characterized by a low magnesium concentration were at increased risk of all-cause mortality (model 1) but this increased risk appeared to be associated with higher FGF23 concentrations compared to the higher magnesium quarters (model 2). Further studies are warranted to investigate if magnesium is a modifiable risk factor, and if the relationship between magnesium and FGF23 concentrations could lead to the development of new management strategies in feline CKD.

Example 2: Benefits of Oral Magnesium Supplementation in the Management of Feline Chronic Kidney Disease (CKD)—Mineral and Bone Disorder (MBD)

Data from a retrospective study among 160 cats with chronic kidney disease (CKD) showed that plasma magnesium concentrations were associated with survival. Both low and high magnesium concentrations at diagnosis of CKD had higher hazard ratios than normal concentrations in univariable Cox regression analysis. However, while high magnesium levels remained independently associated with decreased survival times, the increased mortality risk of the low magnesium group seemed to be related to significantly higher fibroblast growth factor 23 (FGF23) concentrations in this group (FIG. 1) such that FGF23 but not low serum magnesium stayed in the multivariate model. Linear regression showed that total magnesium is an independent predictor of FGF23 concentration. Prospective studies were warranted to investigate if magnesium supplementation can reduce FGF23 levels and improve survival time in cats with low magnesium concentrations at diagnosis of CKD. A study was therefore conducted to determine whether oral magnesium supplementation reduces serum FGF23, which can be a novel approach to managing bone and mineral disorders in feline CKD patients.

Aims of the Study

The primary aim was to determine whether oral magnesium supplementation to cats with a diagnosis of azotemic CKD and concurrent low plasma magnesium concentration reduces plasma FGF23 concentration in these animals.

Secondary aims were 1) to determine if oral magnesium supplementation improves magnesium status, and to what extent; 2) assessment of associations between magnesium supplementation and changes in other clinicopathological variables (phosphate, ionized calcium, PTH, calcitriol, potassium, systolic blood pressure); and 3) evaluation of the occurrence of possible side effects of magnesium supplementation (i.e., hypermagnesemia, struvite urolithiasis, diarrhea).

Study Protocol

Enrolment

Cats with azotemic CKD and hypomagnesaemia were recruited into a clinical trial. Screening pre-treatment involved: 1) Plasma biochemistry (including total thyroxine and total magnesium), hematocrit and total protein; 2) Urinalysis; 3) Systolic blood pressure measurement; and 4) Plasma FGF23 and PTH measurement.

Inclusion criteria were 1) diagnosis of stable azotemic CKD IRIS stage 2 or 3; 2) Plasma total magnesium concentration <0.80 mmol/L; and 3) stable diet for the last 2 months (no changes in diet allowed during the study)

Exclusion criteria were 1) hyperthyroidism (total thyroxine concentration <40 nmol/L); 2) a diagnosis of hypertension; 3) struvite crystals identified on urinalysis (if urine is concentrated, it is common to observed struvite crystals; exclusion applied only if large amounts of crystals were present); 4) FLUTD within the past year; or 5) use of intestinal phosphate binders.

Treatment

With owner consent, cats received oral magnesium supplementation, consisting of 63.6 to 90.1 milligrams elemental magnesium per day with food preferably as magnesium glycinate.

Particularly, cat diet was supplemented with 100 mg Mg Glycinate per kilogram of body weight, which is equivalent to 14.1 mg Mg/kg. For example, a 5 kg cat requires about 200 kcal per day, which should consume a supplementation of 70 mg/1000 kcal per day. The magnesium supplement was added upon the existing magnesium in the cat food, which resulted in a range of 260-330 mg Mg/1000 kcal in feline diets.

Follow-Up

Assessment was made after 4 to 6 weeks of oral magnesium supplementation. During this visit, systolic blood pressure measurement, and blood and urine samples were obtained. Participation was terminated if 1) the cat refused to take magnesium supplementation; 2) the cat refused to eat Renal diet when magnesium was supplemented, such that less than 50% of the daily calorific intake was made up of Renal diet; 3) plasma total magnesium concentration exceeded 1.0 mmol/L; 4) magnesium ammonium phosphate crystals were noted in urine sediment; 5) the cat developed diarrhea; 6) the cat developed a significant medical condition other than azotemic CKD, which required additional treatment or warrants euthanasia; 7) adverse effects were observed that require cessation of feeding the diet, for example ionized hypercalcemia with concurrent clinical signs; or 8) the owner failed to bring the cat in for follow-up appointments.

Analysis

The effect of oral magnesium supplementation on magnesium and FGF23 status were determined by 1) change in plasma total magnesium concentration relative to baseline and 2) change in plasma FGF23 concentration relative to baseline.

The effects of oral magnesium supplementation on other parameters involved in feline CKD were determined by 1) change in plasma intact PTH concentration relative to baseline; 2) change in plasma calcitriol concentration relative to baseline; 3) change in plasma phosphate concentration relative to baseline; 4) change in systolic blood pressure relative to baseline; and 5) change in whole blood potassium concentration relative to baseline

Results

FIG. 1 illustrates plasma FGF23 concentrations in cats with azotemic CKD IRIS stage 2-3 categorized in quartiles according to plasma total magnesium concentration. The median total magnesium concentration was 0.84 [0.75, 0.92] mmol/L. Cats in the lowest magnesium quartile had a significantly higher FGF23 concentration (2008.7 [762.1, 8194.4] pg/mL) compared to all three upper quarters, which did not significantly differ from each other (MgQ2: 895.3 [455.0, 1948.2]; MgQ3: 493.9 [344.2, 2035.5]; MgQ4: 477.8 [316.9, 975.7] pg/mL. P<0.005). The dotted line represents the upper limit of the reference range of plasma FGF23 in geriatric cats (700 pg/mL). The Y-axis of FIG. 1 is on a logarithmic scale.

Figure 2A:
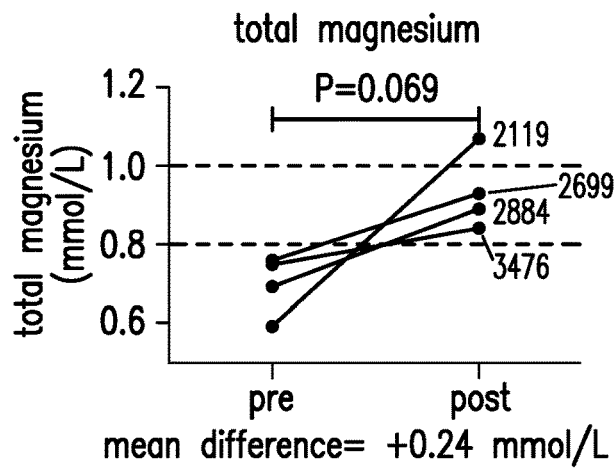
FIGS. 2A-2C show the effects of magnesium supplement on total magnesium, FGF23 and phosphate in blood. The dotted line represents the upper limit of the reference range of plasma FGF23 in geriatric cats (700 pg/mL).
Figure 2B:
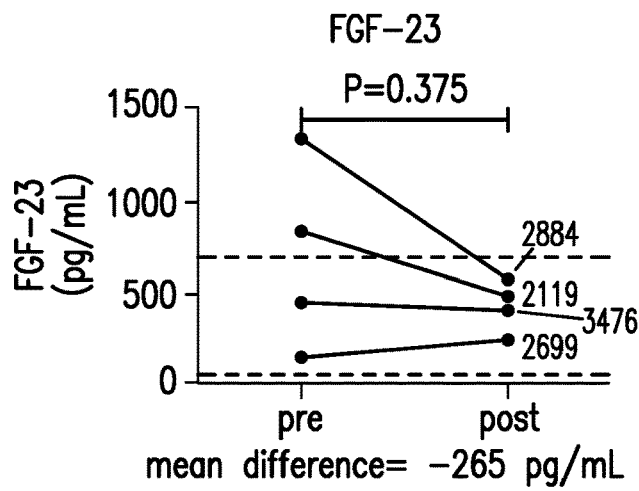
Figure 2C:
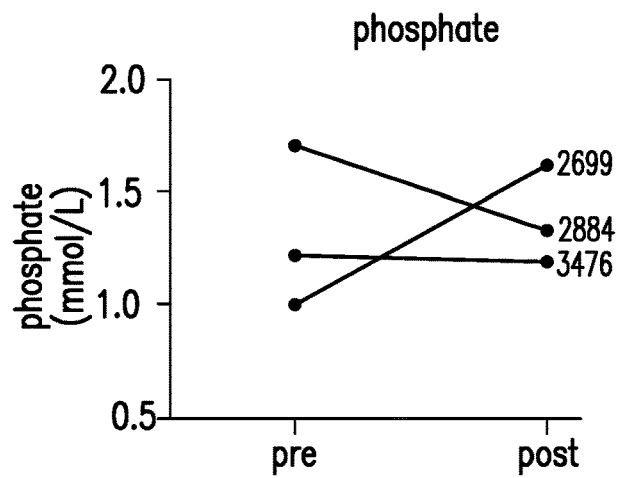
Figures 3A, 3B, 3C:
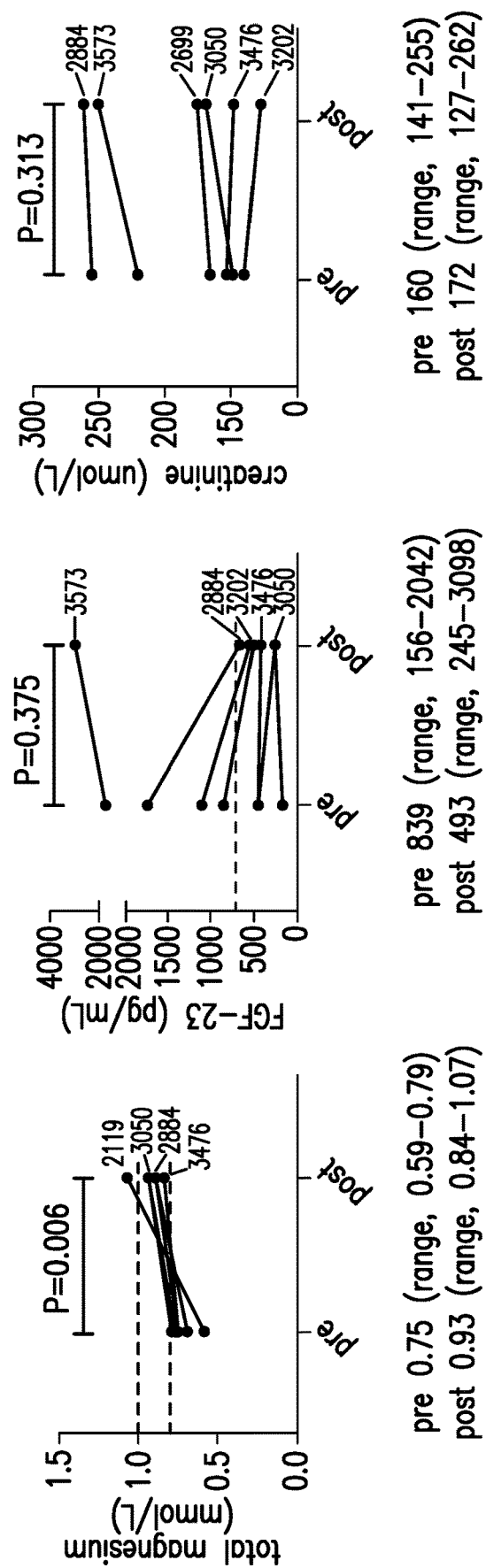
FIGS. 3A-3I show the effects of magnesium supplement on total magnesium (A), FGF23 (B), creatinine (C), symmetric dimethylarginine (SDMA) (D), phosphate (E), systolic blood pressure (F), potassium (G), calcium (H) and parathyroid hormone (PTH) (I) in cats with azotemic CKD IRIS stage 2-3.
Figures 3D, 3E, 3F:
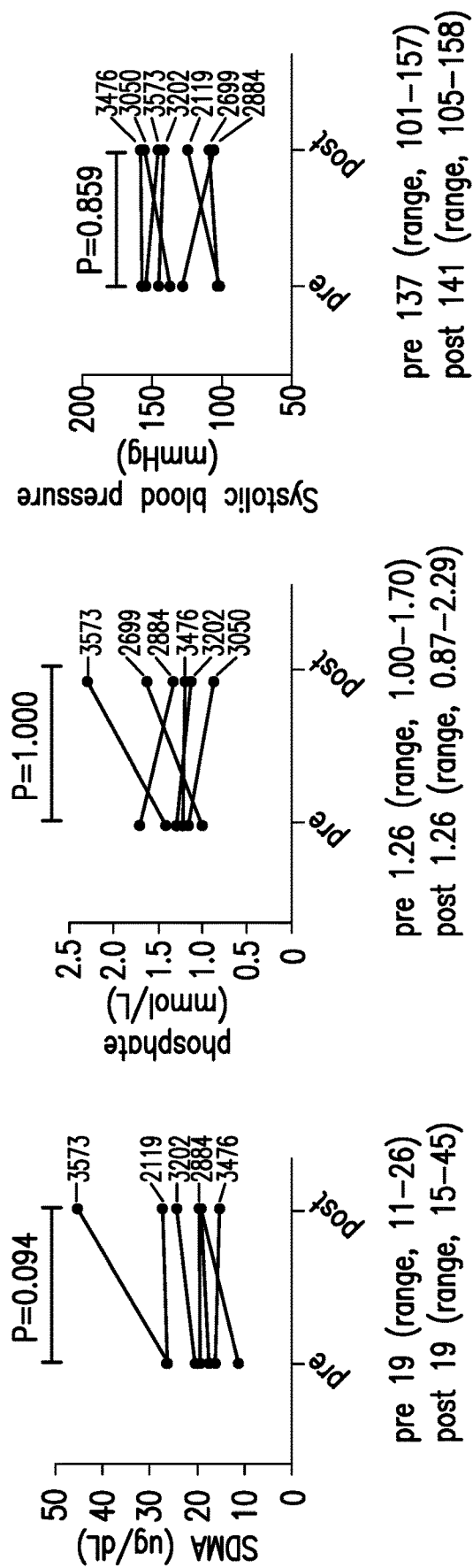
Figures 3G, 3H, 3I:
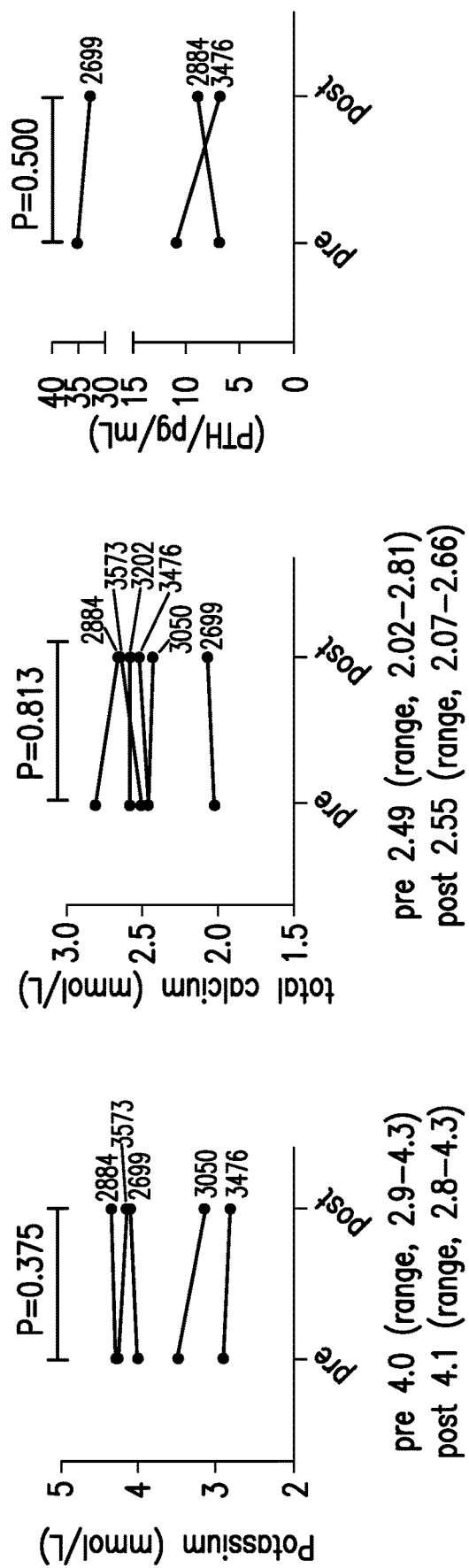

The effects of magnesium supplement on total magnesium, FGF23 and phosphate in blood samples of cats with azotemic CKD IRIS stage 2-3 are shown in FIGS. 2A-2C. FIG. 2A shows total serum Mg before and after supplementation in 4 cats. FIG. 2B shows serum FGF23 before and after Mg supplementation. Mg supplementation was associated with a strong decrease of FGF23 in 3 out of 4 cats. FGF23 was a known marker of serum phosphorus accumulation and decreasing FGF23 correlated to reduce the progression of renal disease. FIG. 2C shows serum phosphate before and after supplementation.

FIGS. 3A-3I further show the effects of magnesium supplement on total magnesium (A), FGF23 (B), creatinine (C), symmetric dimethylarginine (SDMA) (D), phosphate (E), systolic blood pressure (F), potassium (G), calcium (H) and parathyroid hormone (PTH) (I) in cats with azotemic CKD IRIS stage 2-3.

Example 3—Observations on the Prognostic Importance of Plasma Total Magnesium in a Cohort of Cats with Azotemic Chronic Kidney Disease The present Example investigates the prevalence and risk factors for magnesium disorders in cats with azotemic CKD, the relationship of plasma tMg with FGF-23 and other clinicopathological variables, and the prognostic significance of magnesium disorders for all-cause mortality and renal function decline in a cohort of cats with azotemic CKD.

Methods

Subjects

Cats were identified from the records of geriatric cat clinics held at two first opinion practices in central London (People's Dispensary for Sick Animals in Bow and Beaumont Sainsbury Animal Hospital in Camden). Client-owned cats≥9 years old visited these clinics for general health screening, and those diagnosed with azotemic CKD subsequently for management of their disease. Cats enrolled in this study were part of a larger observational cohort for which owner consent was obtained and approval of the Ethics and Welfare Committee of the Royal Veterinary College had been granted.

A group of 120 apparently healthy cats seen between September 2001 and September 2013 was selected to establish a reference interval for plasma tMg in older cats. Cats were considered apparently healthy if no significant abnormalities were detected in the clinical history, physical examination, or blood and urine examination, and if no medications had been prescribed. For inclusion, a stored heparinized plasma sample had to be available for measurement of tMg.

A cohort of cats diagnosed with azotemic CKD between August 1999 and July 2013 was selected to explore the clinical significance of baseline plasma tMg in feline CKD. Criteria for a diagnosis of azotemic CKD were plasma creatinine concentration≥2 mg/dL in conjunction with a urine specific gravity (USG)<1.035, or plasma creatinine concentration≥2 mg/dL on 2 consecutive occasions 2-4 weeks apart. To be enrolled, data on plasma FGF-23 concentration and a stored residual heparinized plasma sample for measurement of tMg had to be available from the time of diagnosis of CKD. Cats with clinical signs of hyperthyroidism, plasma total thyroxine concentration>40 nmol/L, medical treatment for hyperthyroidism, diabetes mellitus, or treatment with corticosteroids were excluded from all analyses. Cats receiving amlodipine besylate for treatment of systemic hypertension were included.

Data Collection

Clinic visits consisted of history and physical examination, systolic blood pressure (SBP) measurement, and blood and urine collection. Baseline data obtained at the date of diagnosis of azotemic CKD, were retrieved from electronic clinical records, and included age, breed, sex, body weight, body condition score (BCS), systolic blood pressure (SBP), plasma total thyroxine concentration, PCV, routine plasma biochemical variables (total protein, albumin, globulin, creatinine, sodium, potassium, chloride, phosphate, and total calcium concentrations), ionized calcium concentration, venous bicarbonate ($HCO_3^-$) and pH values, plasma calcidiol, calcitriol, FGF-23 and PTH concentrations, USG, urine culture result, urine protein-to-creatinine ratio (UPC), and fractional excretion (FE) of magnesium value. The date of death and whether progression of azotemia occurred (defined below) were also documented. Anomalous or missing data from the electronic records were verified by consulting the physical patient records. Severity of CKD and phosphate status were classified according to International Renal Interest Society (IRIS) guidelines.[88] Systolic BP had been assessed using a Doppler method[89] and indirect ophthalmoscopy was performed in all cats where SBP>160 mmHg was identified. Systemic hypertension was defined as SBP>170 mmHg on at least 2 occasions 1-2 weeks apart, or a single SBP>160 mmHg in association with ocular target organ damage.

Blood samples had been obtained via jugular venipuncture and urine samples via cystocentesis. Total magnesium was measured in residual heparinized plasma, which had been stored at −80° C., by the laboratory that also had performed the routine biochemical analysis.[90] FGF-23 and PTH had been measured in EDTA plasma using validatee[4,32] ELISA[91] and immunoradiometric[92] assays respectively. For measurement of FGF-23, samples had been diluted with the zero standard to achieve a reading on the standard curve. The PTH assay had a limit of detection of 5.2 pg/mL,[32] and samples with a concentration below this value were assigned an arbitrary PTH concentration of 2.6 pg/mL. Results of ionized calcium, venous blood gasses, and vitamin D-metabolites were available only for some cats. Ionized calcium concentration and blood gasses had been measured in non-heparinized whole blood using a point-of-care analyzer[93] directly following venipuncture. Vitamin D-metabolites had been measured at an external laboratory.[94] Urinalysis included in-house measurement of USG by refractometry, dipstick analysis, and urine sediment microscopic examination. Urine biochemistry was performed by a commercial laboratory. Fractional excretion values were determined using the spot sample approach.[33]

Statistical Analysis

Statistical analyses were performed using statistical software packages.[95] For all reported analyses two-sided tests of significance were carried out with an alpha level of ≤0.05 defining statistical significance. Continuous clinical data are presented as mean (SD) or as median [$25^{th}$, $75^{th}$ percentiles] as appropriate. The distribution of numerical variables was assessed for normality by Shapiro-Wilk test and visual inspection of Q-Q plots. Baseline characteristics between groups were compared using either independent samples t-test (2 groups) or one-way ANOVA with Bonferroni post hoc comparison (≥3 groups) for continuous variables with a normal distribution, or using Mann-Whitney U tests (2 groups) or Kruskal-Wallis test followed by Mann-Whitney U tests with Bonferroni correction (≥3 groups) for variables with a skewed distribution. Proportions were compared using Fisher's exact test.

Prevalence and Factors Associated with Magnesium Disorders

Cats were categorized in 3 groups based on the lower and upper limits of the derived reference interval for plasma tMg in older cats, which was calculated using the parametric method (i.e. mean±2SD). The prevalence of hypomagnesemia and hypermagnesemia at diagnosis of azotemic CKD were calculated using this reference interval, baseline characteristics between the 3 magnesium groups compared, and binary logistic regression performed to explore risk factors for either hypomagnesemia or hypermagnesemia. Variables significantly associated with these conditions were entered into a multivariable binary logistic regression model. The final model was derived by manual backward elimination. Goodness of fit of the model was assessed with Hosmer-Lemeshow test. Results are reported as odds ratio (OR; 95% confidence interval [CI]).

Association of Plasma Total Magnesium with Plasma FGF-23 and Other Clinicopathological Variables Plasma FGF-23 concentrations were compared between hypomagnesemic, normomagnesemic, and hypermagnesemic cats within each IRIS stage, as well as between cats with plasma tMg below and above the median (<2.04 mg/dL and ≥2.04 mg/dL) within normophosphatemic and hyperphosphatemic subgroups (based on IRIS targets for plasma phosphate for each stage) of cats with IRIS stage 2 and 3 CKD.

The Pearson correlation coefficient (r) was computed to evaluate the association between plasma tMg and log-transformed FGF-23 concentration (logarithmus naturalis [ln]). Partial correlation was performed to measure the strength of association between these two variables with the confounding effects of ln[creatinine] and ln[phosphate] removed, both known predictors of plasma FGF-23.[4]

Univariable general linear models adjusted for IRIS stage were constructed to explore what variables were associated with plasma tMg as a continuous variable. Age, weight, PCV, plasma albumin, sodium, potassium, chloride, total calcium, ln[FGF-23], ln[PTH], ln[creatinine], ln[phosphate] concentrations, and ln[UPC] were assessed as continuous covariates. IRIS stage and hypertensive status were entered as fixed factors. Covariates associated with plasma tMg with an alpha level<0.10 were assessed for statistical interaction with IRIS stage and entered into a multivariable linear regression model including any significant interaction terms. The final regression model was derived by backward elimination. The assumptions of normality and of linear relationship between variables were checked by visual inspection of histograms of the residuals and of scatter plots of the residuals against the fitted values. Results are reported as regression coefficient (β; 95% CI).

Association of Plasma Total Magnesium with Survival

To assess if plasma tMg was related to survival, all enrolled cats were included in a survival analysis for which the date of diagnosis of azotemic CKD was designated as baseline, all-cause mortality was the event of interest, and censoring occurred for cats that were lost to follow-up or that were still alive on 1 Jul. 2016. Cats lost to follow-up were censored on the last date known to be alive. The Kaplan Meier curve of the normomagnesemic group was compared with those of the hypomagnesemic and hypermagnesemic cats using log-rank test, and hazard ratios (HR) were calculated with univariable time-invariant Cox proportional hazard analysis. To adjust for possible confounding factors, associations with survival of the following baseline variables were assessed with univariable Cox regression analysis: plasma tMg, creatinine, phosphate, total calcium, sodium, chloride, potassium, albumin, FGF-23, and PTH concentrations, age, PCV, body weight, BCS, hypertension status, USG, and UPC. Plasma PTH was log-transformed because of its strongly skewed distribution. Continuous variables were categorized if the assumption of proportional hazards, evaluated by inspection of Kaplan-Meier curves and assessment of statistical interaction of each variable with time, were not met. Grouping was based on clinically relevant margins if possible (plasma tMg, hypertension status, BCS), or terciles (phosphate, FGF-23, sodium, USG, weight). No missing data imputation was performed. Variables associated with survival with an alpha level<0.10 were assessed for interaction with magnesium status, and subsequently entered multivariable analysis together with any statistically significant interaction term (P<0.05). The final multivariable model was derived by manual backward elimination. The overall fit of the Cox model was checked by visual inspection of a Cox-Snell residual plot. Results are reported as HR (95% CI).

Given the nonlinear relationship with mortality rates, plasma tMg was analyzed as a categorical variable divided on the lower and upper limits of the derived reference interval in the main analysis. To explore the effect on survival of plasma tMg on a continuous scale, a sub-analysis was performed. Cats were divided by a median split of tMg, and instead of as a categorical variable, tMg entered in the fully-adjusted Cox model as a continuous variable.

Additionally, a pre-defined interaction between plasma magnesium concentration and phosphate status in association with all-cause mortality was explored. Cats with IRIS stage 2 and 3 CKD were divided based on phosphate status according to IRIS phosphate target guidelines,[96] and by a median split of plasma tMg. This resulted in the following 4 categories: normophosphatemic-lower magnesium (NP-LM: IRIS normophosphatemic; plasma magnesium<2.04 mg/dL), normophosphatemic-higher magnesium (NP-HM: IRIS normophosphatemic; plasma magnesium≥2.04 mg/dL), hyperphosphatemic-lower magnesium (HP-LM: IRIS hyperphosphatemic; plasma magnesium<2.04 mg/dL), and hyperphosphatemic-higher magnesium (HP-HM: IRIS hyperphosphatemic; plasma magnesium≥2.04 mg/dL). Statistical interaction between magnesium and phosphate in relation to survival was explored by comparing hazards of the 4 phosphate-magnesium groups using univariable Cox regression. The NP-HM group was chosen as the joint reference category of no exposure to calculate the relative excess risk due to interaction (RERI, i.e. the difference between the expected risk and the observed risk) of the HP-LM group.[34,97]

Association of Plasma Total Magnesium with Progression of CKD

Whether magnesium status was associated with CKD progression was examined using binary logistic regression. Cats were categorized into 2 groups: a progressive CKD group that showed a >25% increase in plasma creatinine concentration within the first 12 months of diagnosis, and a stable CKD group that did not show an increase. Only stable cats with follow-up of ≥12 months were included in this analysis. Magnesium status, plasma creatinine, phosphate, total calcium, potassium, albumin, ln[FGF-23], and ln[PTH], age, PCV, body weight, BCS, hypertension status, USG, and UPC entered univariable binary logistic regression. Variables associated with progressive disease with an alpha level<0.10 in univariable analysis entered multivariable regression. The final model was derived by manual backward elimination. Goodness of fit was assessed with Hosmer-Lemeshow test. Results are reported as OR (95% CI). The pre-defined interaction between plasma magnesium concentration and phosphate status in association with progression of CKD was explored by comparing the ORs of the 4 phosphate-magnesium groups (defined above) using univariable logistic regression.

Results

To explore associations of plasma total magnesium concentration with plasma FGF-23, all-cause mortality, and disease progression in cats with azotemic CKD, records of 174 client-owned cats with IRIS stage 2-4 CKD were analyzed. Possible associations of baseline plasma total magnesium concentration with FGF-23 concentration and risks of death and progression were explored using, respectively, linear, Cox, and logistic regression in a cohort of cats with azotemic CKD from general practice (1999-2013). The results indicate that plasma total magnesium concentration (reference interval, 1.73-2.57 mg/dL) was inversely associated with plasma FGF-23 when controlling for plasma creatinine concentration (partial correlation coefficient, −0.50; P<0.001). Hypomagnesemia was observed in 12% (20/174) of cats, and independently associated with increased risk of death (adjusted hazard ratio, 2.40; 95% confidence interval [CI], 1.18-4.86; P=0.016). The unadjusted associations of hypermagnesemia (prevalence, 6%; 11/174 cats) with survival (hazard ratio, 2.88; 95% CI, 1.54-5.38; P=0.001), and hypomagnesemia with progressive CKD (odds ratio, 17.68; 95% CI, 2.04-153.59; P=0.009) lost significance in multivariable analysis.

Determination of a 95% Reference Interval for Plasma Total Magnesium Concentration in Older Cats The reference population consisted of 53 male cats and 67 female cats, with 1 entire male and 1 entire female. Cats were of the following breeds: domestic shorthair (n=97), domestic longhair (n=12), Burmese (n=4), 2 each of Persian, British shorthair and Russian blue, and 1 British blue. Further characteristics can be found in Table 1. The distribution of plasma tMg was determined to be Gaussian, with a mean concentration of 2.15 (SD, 0.209) mg/dL, resulting in a 95% reference interval of 1.73-2.57 mg/dL (0.71-1.06 mmol/L).

TABLE 1

| Variable (reference interval) | Median [25$^{th}$, 75$^{th}$ Percentile] | n |
|---|---|---|
| Age (years) | 12.4 [11.1, 14.0] | 120 |
| Weight (kg) | 4.51 [3.81, 5.20] | 120 |

TABLE 1-continued

| Variable (reference interval) | Median [25th, 75th Percentile] | n |
|---|---|---|
| Creatinine (0.23-2.00 mg/dL) | 1.45 [1.32, 1.65] | 120 |
| USG (≥1.035) | 1.048 [1.040, 1.058] | 80 |
| Phosphate (2.79-6.81 mg/dL) | 3.85 [3.28, 4.30] | 120 |
| Total calcium (8.2-11.8 mg/dL) | 9.8 [9.4, 10.2] | 120 |
| Total protein (6.0-8.0 g/dL) | 7.7 [7.3, 8.0] | 120 |
| Albumin (2.5-4.5 g/dL) | 3.3 [3.0, 3.4] | 120 |
| PCV (30-45%) | 38 [35, 41] | 120 |
| Sodium (145-157 mEq/L) | 152 [152, 154] | 120 |
| Potassium (3.5-5.5 mEq/L) | 3.9 [3.7, 4.2] | 120 |
| Chloride (100-124 mEq/L) | 119 [117, 121] | 120 |
| SBP (<160 mmHg) | 136 [120, 150] | 120 |

Table 1. Characteristics of 120 apparently healthy cats ≥9 years from which the reference interval for plasma total magnesium concentration was derived. USG, urine specific gravity; PCV, packed cell volume; SBP, systolic blood pressure.

Plasma Total Magnesium in Cats with Azotemic CKD

Between August 1999 and July 2013, a total of 517 cats were diagnosed with azotemic CKD, of which 96 cats were excluded for the following reasons: concurrent hyperthyroidism (n=79), not meeting the study criteria for diagnosis of CKD (n=16), or prednisolone administration (n=1). Of the 421 eligible cats, 88 cats had no residual plasma sample available for measurement of tMg, 157 cats lacked baseline information on plasma FGF-23 concentration, and 2 samples were grossly hemolyzed. Thus, 174 cats were enrolled in this study, some of which had been included in previous studies.[5,8] No significant differences were observed between baseline characteristics of the 174 included cats and of the 247 eligible cats that were excluded from analysis because of lack of a residual plasma sample or plasma FGF-23 measurement (data not shown).

The study population consisted of 88 females, of which 1 was entire, and 86 males, of which 3 were entire. Domestic shorthair was the most common breed (n=127), followed by domestic longhair (n=20), Persian (n=10), Burmese (n=7), British shorthair (n=2), Siamese (n=2), and 1 each of Abyssinian, American shorthair, Chinchilla, Ocicat, Russian blue, and Tiffany. According to the International Renal Interest Society (IRIS) staging system, 114 cats had stage 2, 50 cats stage 3, and 10 cats stage 4 CKD. The study population was older than the group of cats from which the reference interval for plasma tMg was derived (mean, 14.4 years; SD, 3.2 versus 12.7 years; SD, 2.2, respectively).

Prevalence and Factors Associated with Magnesium Disorders

Figure 4:
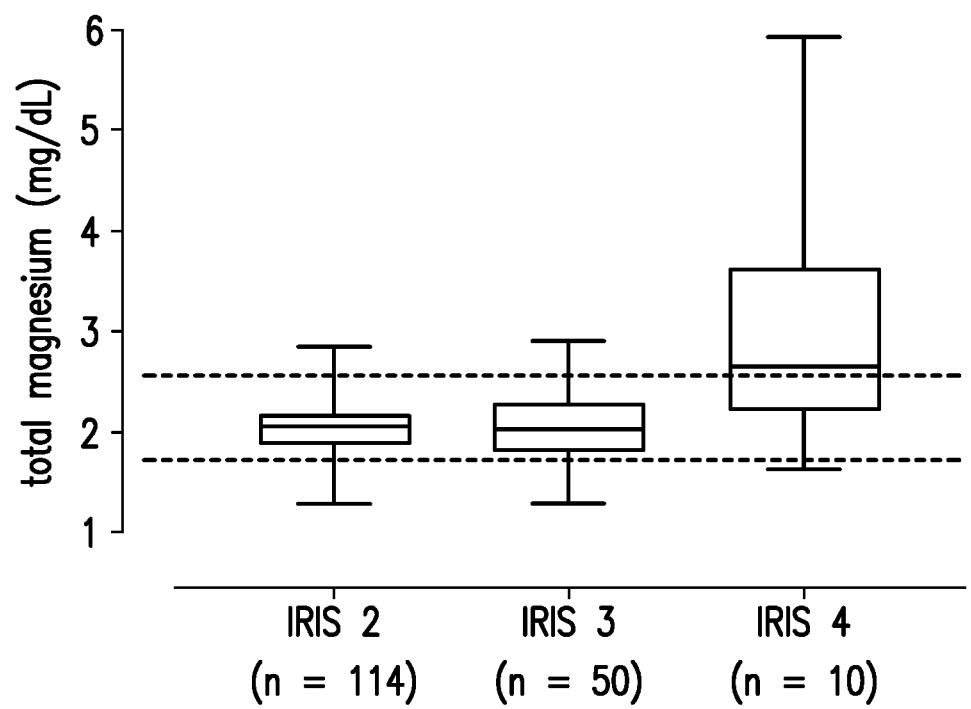
FIG. 4 shows plasma total magnesium concentration in cats with IRIS stages 2 to 4 CKD. Significantly higher plasma magnesium concentrations were observed in cats with IRIS stage 4 CKD (mean, 3.01 mg/dL; SD, 1.206; P<0.001) compared to cats with IRIS stage 2 (mean, 2.04 mg/dL; SD, 0.261) and 3 CKD (mean, 2.04 mg/dL; SD, 0.361). The prevalence (95% CI) of hypomagnesemia was 9% (4-14), 18% (7-29), and 10% (0-27) respectively in IRIS stages 2, 3, and 4. The prevalence of hypermagnesemia was significantly higher in IRIS stage 4 (50%; 95% CI, 19-81; P<0.001) compared to IRIS stages 2 (3%; 95% CI, 0-6) and 3 (6%; 95% CI, 0-13). The boxes represent medians with $25^{th}$ and $75^{th}$ percentiles, the whiskers represent ranges. Dotted lines mark the lower and upper limits of the reference interval for plasma total magnesium (1.73-2.57 mg/dL).

The median plasma tMg of the study population was 2.07 [1.87, 2.26] mg/dL (range, 1.29-5.79). Twenty of 174 cats were diagnosed with hypomagnesemia (prevalence, 12%; 95% CI, 7-17), and 11 cats with hypermagnesemia (prevalence, 6%; 95% CI, 3-10). Hypermagnesemia was predominantly observed in cats with IRIS stage 4 (FIG. 4). Baseline characteristics of cats with hypomagnesemia, normomagnesemia, and hypermagnesemia are shown in Table 2.

Risk factors associated with magnesium disorders can be found in Table 3.

Multivariable regression showed that higher plasma ln[FGF-23] (OR, 2.07; 95% CI, 1.48-2.90; P<0.001) and a diagnosis of systemic hypertension (OR, 4.24; 95% CI, 1.41-12.78; P=0.010) were independently associated with hypomagnesemia in cats with CKD (Nagelkerke $R^2$, 0.30). The median plasma tMg of the subgroup of cats with systemic hypertension was 1.97 [1.69, 2.14] mg/dL compared to 2.09 [1.90, 2.29] mg/dL in the normotensive group (P=0.004). No multivariable analysis was performed for hypermagnesemia because of the relatively low number of hypermagnesemic cases.

TABLE 2

| Variable (reference interval) | Hypomagnesemic (n = 20) | | Noromagnesemic (n = 143) | | Hypermagnesemic (n = 11) | |
|---|---|---|---|---|---|---|
| Total magnesium (1.73-2.57 mg/dL) | 1.57 [1.41, 1.66] | 20 | 2.07 [1.92, 2.24] | 143 | 2.87 [2.70, 3.60] | 11 |
| Age (years) | 16.6 [15.0, 18.2][a] | 19 | 14.8 [12.0, 16.2] | 130 | 12.0 [9.8, 15.0][b] | 11 |
| Weight (kg) | 2.98 [2.51, 3.56][a] | 19 | 3.92 [3.14, 4.61][b] | 142 | 3.63 [3.25, 4.20] | 9 |
| BCS (1-9) | 3 [3, 4] | 10 | 4 [3, 5] | 90 | 3 [3, 5] | 5 |
| Sex (male, n [%]) | 7 (35) | 20 | 72 (50) | 143 | 7 (64) | 11 |
| Albumin (2.5-4.5 g/dL) | 3.0 [2.8, 3.3] | 20 | 3.1 [2.9, 3.3] | 143 | 3.0 [2.9, 3.3] | 11 |
| Calcidiol (65-170 nmol/L) | — | 0 | 141 [122, 184] | 14 | 105 [−] | 2 |
| Calcitriol (90-342 pmol/L) | — | 0 | 418 [351, 463] | 13 | 362 [−] | 2 |
| Chloride (100-124 mEq/L) | 117 [116, 119] | 20 | 118 [116, 120] | 143 | 117 [114, 122] | 11 |
| Creatinine (0.23-2.00 mg/dL) | 2.85 [2.32, 4.03][a] | 20 | 2.48 [2.25, 2.96][a] | 143 | 4.82 [2.65, 5.47][b] | 11 |
| FGF-23 (56-700 pg/mL) | 4950 [1931, 15893][a] | 20 | 637 [351, 1941][b] | 143 | 2658 [684, 8582] | 11 |
| FGF-23 excess (n [%]) | 18 (90)a | 20 | 68 (48)a | 143 | 8 (73) | 11 |
| Globulin (2.5-4.5 g/dL) | 4.4 [4.1, 4.9][a] | 20 | 4.7 [4.3, 5.3] | 143 | 4.8 [4.5, 6.2][b] | 11 |
| $HCO_3^-$ (17-24 mEq/L) | 21 [19, 25] | 5 | 20 [18, 22] | 37 | 20 [−] | 3 |
| Ionized calcium (1.19-1.37 mmol/L) | 1.28 [1.16, 1.34] | 5 | 1.30 [1.26, 1.33] | 38 | 1.16 [−] | 3 |
| PCV (30-45%) | 30 [24, 34] | 20 | 34 [30, 37] | 141 | 32 [23, 34] | 11 |

TABLE 2-continued

| Variable (reference interval) | Hypomagnesemic (n = 20) | | Noromagnesemic (n = 143) | | Hypermagnesemic (n = 11) | |
|---|---|---|---|---|---|---|
| Venous pH (7.21-7.44) | 7.35 [7.32, 7.38] | 5 | 7.33 [7.29, 7.38] | 37 | 7.33 [–] | 3 |
| Phosphate (2.79-6.81 mg/dL) | 5.51 [4.47, 6.93]$^a$ | 20 | 4.43 [3.75, 5.39]$^b$ | 143 | 6.16 [4.46, 9.54]$^a$ | 11 |
| Hyperphosphatemia (% [n]) | 14 (70) | 20 | 64 (45) | 43 | 7 (64) | 11 |
| Potassium (3.5-5.5 mEq/L) | 3.9 [3.7, 4.4] | 20 | 4.1 [3.7, 4.3] | 143 | 4.0 [3.4, 4.8] | 11 |
| Hypokalemia (n [%]) | 2 (10) | 20 | 17 (12) | 143 | 3 (27) | 11 |
| Hyperkalemia (n [%]) | 0 (0) | 20 | 0 (0) | 143 | 1 (9) | 11 |
| PTH (2.6-17.6 pg/mL) | 46.3 [12.5, 93.0]$^a$ | 17 | 15.2 [6.5, 31.2]$^b$ | 138 | 25.0 [11.7, 81.9] | 10 |
| SRHPT (n [%]) | 12 (71) | 17 | 67 (49) | 138 | 6 (60) | 10 |
| SBP (<160 mmHg) | 153 [134, 163] | 20 | 142 [128, 156] | 143 | 136 [128, 150] | 11 |
| Hypertension (n [%]) | 9 (45)$^a$ | 20 | 26 (18)$^b$ | 143 | 2 (18) | 11 |
| Sodium (145-157 mEq/L) | 154 [153, 155] | 20 | 153 [152, 155] | 143 | 151 [150, 156] | 11 |
| Total calcium (8.2-11.8 mg/dL) | 10.7 [10.1, 11.0]$^a$ | 20 | 10.2 [9.7, 10.5] | 143 | 9.6 [9.4, 10.4]$^b$ | 11 |
| Total protein (6.0-8.0 g/dL) | 7.6 [7.1, 7.9]$^a$ | 20 | 7.8 [7.5, 8.3]$^b$ | 143 | 8.2 [7.6, 9.1]$^b$ | 11 |
| UPC (<0.20) | 0.31 [0.27, 0.61]$^a$ | 13 | 0.17 [0.12, 0.32]$^b$ | 115 | 0.50 [0.23, 1.19]$^a$ | 9 |
| UPC <0.20 (n [%]) | 1 (8)$^a$ | 13 | 70 (61)$^b$ | 115 | 1 (11)$^a$ | 9 |
| UPC >0.40 (n [%]) | 5 (39) | 13 | 21 (18)$^a$ | 115 | 5 (56)$^b$ | 9 |
| USG (≥1.035) | 1.016 [1.014, 1.020] | 19 | 1.018 [1.016, 1.021] | 136 | 1.016 [1.014, 1.018] | 10 |
| FE magnesium (%) | 6.8 [4.0, 8.6]$^a$ | 7 | 5.0 [2.2, 5.4]$^b$ | 12 | — | 0 |
| Progressive CKD (n [%]) | 7 (88)$^a$ | 8 | 19 (20)b | 67 | 3 (75) | 4 |
| Survival time (days) | 147 [52, 328] | 19 | 559 [205, 879]$^b$ | 122 | 125 [50, 423]$^a$ | 11 |
| Follow-up (days) | 152 [53, 336]$^a$ | 20 | 546 [207, 890]$^b$ | 143 | 125 [50, 423]$^a$ | 11 |
| Year of diagnosis | 2008 [2004, 2011] | 20 | 2009 [2007, 2011] | 143 | 2008 [2003, 2012] | 11 |

Characteristics of cats with azotemic CKD grouped according to magnesium status. Data presented as median [25$^{th}$, 75$^{th}$ percentile] or prevalence (n []+). Rows bearing a different superscript letter are significantly different from one another. BCS, body condition score; FGF-23, fibroblast growth factor 23; HCO$_3^-$, venous bicarbonate; PCV, packed cell volume; PTH, parathyroid hormone; SRHPT, secondary renal hyperparathyroidism; SBP, systolic blood pressure; UPC, urine protein to creatinine ratio; USG, urine specific gravity; FE, fractional excretion.

TABLE 3

| Univariable analysis | n | OR (95% CI) | P |
|---|---|---|---|
| Hypomagnesemia | | | |
| ln[FGF-23] (pg/mL) | 163 | 1.99 (1.46-2.73) | <0.001 |
| Weight (kg) | 161 | 0.25 (0.11-0.55) | 0.001 |
| Diagnosis of hypertension | 163 | 3.68 (1.38-9.79) | 0.009 |
| Phosphate (mg/dL) | 163 | 1.26 (1.05-1.51) | 0.013 |
| ln[PTH] (pg/mL) | 155 | 1.77 (1.13-2.77) | 0.013 |
| PCV (%) | 161 | 0.92 (0.85-0.99) | 0.028 |
| Creatinine (mg/dL) | 163 | 1.48 (1.04-2.12) | 0.032 |
| Age (years) | 149 | 1.20 (1.01-1.42) | 0.033 |
| Total calcium (mg/dL) | 163 | 1.86 (1.03-3.38) | 0.041 |
| Hypermagnesemia | | | |
| Creatinine (mg/dL) | 154 | 2.22 (1.36-2.63) | 0.001 |
| UPC | 124 | 2.72 (1.37-5.37) | 0.004 |
| Phosphate (mg/dL) | 154 | 1.33 (1.09-1.61) | 0.006 |
| PCV (%) | 152 | 0.90 (0.82-0.99) | 0.029 |
| Age (years) | 141 | 0.81 (0.66-0.99) | 0.044 |

Table 3. Univariable binary logistic regression results identifying risk factors for hypomagnesemia (n = 20) and hypermagnesemia (n = 11) in 174 cats with azotemic CKD. Plasma FGF-23 concentration and hypertension status remained independent risk factors for hypomagnesemia in multivariable analysis. No multivariable regression was performed for hypermagnesemia. OR, odds ration; 95% CI, 95% confidence interval; FGF-23, fibroblast growth factor 23; PTH, parathyroid hormone; PCV, packed cell volume; UPC, urine protein to creatinine ratio.

Figure 5:
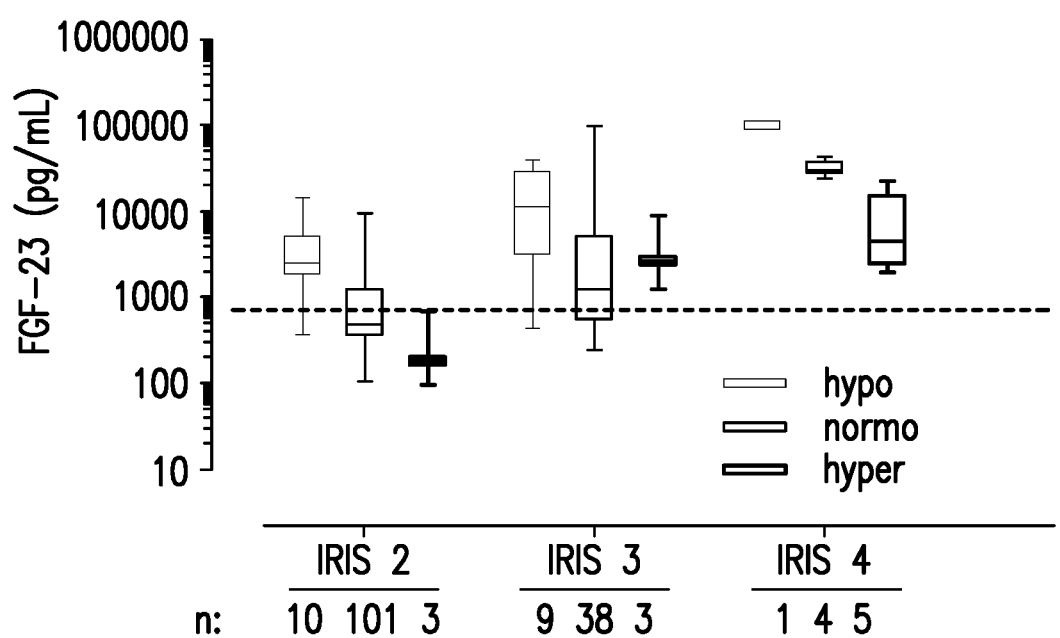
FIG. 5 shows plasma FGF-23 concentrations in cats with IRIS stage 2-4 CKD subdivided by magnesium status. Cats with hypomagnesemia (tMg<1.73 mg/dL) had significantly higher plasma FGF-23 compared to normomagnesemic cats within each stage. The boxes represent medians with $25^{th}$ and $75^{th}$ percentiles, the whiskers represent ranges. The dotted line marks the upper limit of the reference interval for plasma FGF-23 (700 pg/mL).

Association of Plasma Total Magnesium with Plasma FGF-23 and Other Clinicopathological Variables Hypomagnesemic cats had higher FGF-23 concentrations than normomagnesemic cats within each IRIS stage (FIG. 5). Plasma creatinine and phosphate concentrations did not differ significantly between magnesium groups. No correlation was evident between plasma tMg and ln[FGF23] (r, −0.06; P=0.425). However, controlling for plasma creatinine and phosphate resulted in a significant inverse correlation between plasma tMg and FGF-23 (partial r, −0.50; P<0.001). Univariable and multivariable results from the general linear model are presented in Table 4. Fibroblast growth factor 23 was a significant independent predictor of magnesium in all 3 IRIS stages with the strongest effect in stage 4.

Figure 6:
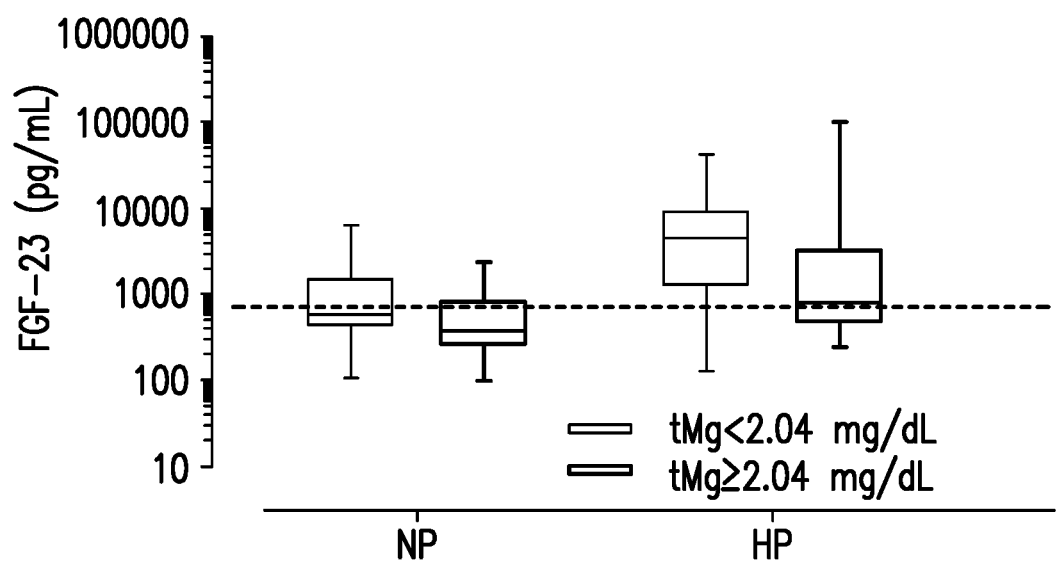
FIG. 6 shows plasma FGF-23 concentrations of normophosphatemic (NP) and hyperphosphatemic (HP) cats with IRIS stage 2 and 3 CKD subdivided by the median plasma tMg concentration (2.04 mg/dL). Plasma FGF-23 was significantly higher in cats with tMg below the median, both in normophosphatemic (P=0.003) and hyperphosphatemic cats (P=0.004). The boxes represent medians with $25^{th}$ and $75^{th}$ percentiles, the whiskers represent ranges. The dotted line marks the upper limit of the reference interval for plasma FGF-23 (700 pg/mL).

In a subgroup analysis of normophosphatemic and hyperphosphatemic cats (based on IRIS targets for plasma phosphate for each stage), plasma FGF-23 concentration was significantly higher in cats with lower plasma tMg compared to cats with higher plasma tMg (FIG. 6). In a general linear model adjusted for IRIS stage, ln[FGF-23] was negatively associated with plasma tMg both in normophosphatemic cats ((3, −0.11; 95% CI, −0.17 to −0.05; P=0.001) and hyperphosphatemic cats ((3, −0.17; 95% CI, −0.24 to −0.10; P<0.001).

TABLE 4

| Variable | β (95% CI) | n |
|---|---|---|
| Univariable analysis* | | |
| IRIS stage | | |
| IRIS 2 | 2.04 (1.97 to 2.11) | 114 |
| IRIS 3 | 2.04 (1.93 to 2.16) | 50 |
| IRIS 4 | 3.01 (2.76 to 3.26) | 10 |
| Age (years) | −0.02 (−0.04 to −0.01) | 160 |
| Weight (kg) | 0.09 (0.02 to 0.15) | 170 |
| ln[PTH] (pg/dL) | −0.05 (−0.10 to 0.00) | 165 |
| Chloride (mEq/L) | 0.01 (−0.00 to 0.03) | 174 |
| Hypertension | −0.19 (−0.33 to −0.04) | 174 |
| ln[Creatinine] (mg/dL) | | |
| IRIS 2 | 0.17 (−0.56 to 0.90) | 114 |
| IRIS 3 | 0.27 (−0.33 to 0.87) | 50 |
| IRIS 4 | 1.57 (1.05 to 2.08) | 10 |
| ln[FGF-23] (pg/mL) | | |
| IRIS 2 | −0.10 (−0.16 to −0.05) | 114 |
| IRIS 3 | −0.06 (−0.11 to −0.00) | 50 |
| IRIS 4 | −0.76 (−0.93 to −0.60) | 10 |
| Albumin (g/dL) | | |
| IRIS 2 | 0.10 (−0.11 to 0.33) | 114 |
| IRIS 3 | 0.27 (−0.02 to 0.57) | 50 |
| IRIS 4 | 2.67 (1.89 to 3.45) | 10 |
| Potassium (mEq/L) | | |
| IRIS 2 | 0.08 (−0.06 to 0.23) | 114 |
| IRIS 3 | 0.02 (−0.17 to 0.21) | 50 |
| IRIS 4 | 0.84 (0.57 to 1.12) | 10 |
| Total calcium (mg/dL) | | |
| IRIS 2 | −0.05 (−0.15 to 0.04) | 114 |
| IRIS 3 | −0.06 (−0.20 to 0.07) | 50 |
| IRIS 4 | −0.97 (−1.32 to −0.63) | 10 |
| Multivariable model (n = 160) | | |
| IRIS stage | | |
| IRIS 2 | 2.83 (1.97 to 3.70) | 106 |
| IRIS 3 | 2.90 (1.59 to 4.20) | 46 |
| IRIS 4 | 10.80 (7.87 to 13.72) | 8 |
| Age (years) | −0.03 (−0.04 to −0.01) | |
| ln[FGF-23] (pg/mL) | | |
| IRIS 2 | −0.11 (−0.16 to −0.06) | |
| IRIS 3 | −0.10 (−0.16 to −0.03) | |
| IRIS 4 | −0.44 (−0.65 to −0.24) | |
| ln[Creatinine] (mg/dL) | | |
| IRIS 2 | 0.63 (0.04 to 1.22) | |
| IRIS 3 | 0.68 (0.08 to 1.29) | |
| IRIS 4 | 1.48 (1.05 to 1.90) | |
| Total calcium (g/dL) | | |
| IRIS 2 | −0.02 (−0.10 to 0.06) | |
| IRIS 3 | −0.06 (−0.17 to 0.05) | |
| IRIS 4 | −0.59 (−0.97 to −0.21) | |

Table 4. General linear model to identify predictors of plasma total magnesium concentration (mg/dL). $R^2$ multivariable model = 0.69. *All variables are accounted for IRIS stage, β, regression coefficient; 95% CI, 95% confidence interval; IRIS, International Renal Interest Society; ln[PTH], log-transformed plasma parathyroid hormone concentration; ln[FGF-23], log-transformed plasma fibroblast growth factor 23 concentration.

Association of Plasma Total Magnesium with Survival

During the total follow-up period of 270.4 patient-years (median, 1.3 [0.5, 2.3] years), 150 cats died, 20 were lost to follow-up, and 4 survived beyond 1 Jul. 2016. Risk of all-cause mortality in the first 12 months after diagnosis of azotemic CKD was 43% (72/167) for the whole population, 35% (48/136) for cats with normomagnesemia at baseline, 80% (16/20) for cats with hypomagnesemia, and 73% (8/11) for those with hypermagnesemia. The incidence rate of all-cause mortality was 0.56 per patient-year for all cats, 0.48 per patient-year for cats with normomagnesemia, and 1.34 per patient-year for cats with hypomagnesemia and cats with hypermagnesemia at diagnosis of CKD.

Figure 7:
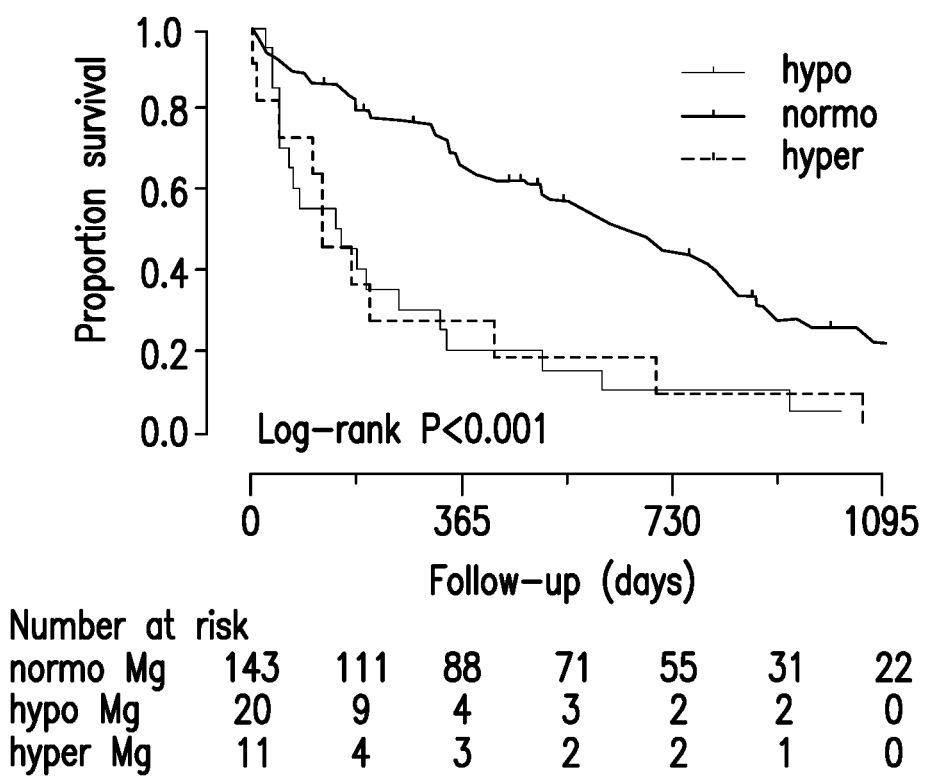
FIG. 7 shows Kaplan-Meier curve illustrating survival in cats with azotemic CKD grouped by magnesium status. Cats with hypomagnesemia (blue curve; 1/20 censored; HR, 2.92; 95% CI, 1.78-4.82; P<0.001) and hypermagnesemia (grey curve; 0/11 censored; HR, 2.88; 95% CI, 1.54-5.38; P=0.001) at diagnosis of azotemic CKD were at increased risk of death compared to normomagnesemic cats (black curve; 23/143 censored). No significant difference in survival was observed between hypomagnesemic and hypermagnesemic cats in univariable analysis (P=0.951). Censored cases are ticked.

Baseline characteristics of the three magnesium categories can be found in Table 5. Censoring occurred in 16% (23/143) of normomagnesemic cats, 5% (1/20) of hypomagnesemic cats, and none of the hypermagnesemic cats. The proportion of censored cases was not significantly different between magnesium categories (P=0.240). Cox regression indicated that hypomagnesemia and hypermagnesemia were associated with increased risk of death (Table 5A and FIG. 7). After adjustment for confounders, hypomagnesemia remained an independent predictor of mortality. No statistically significant differences were observed between baseline characteristics of cats incorporated in the final regression model (n=119) and those of cats omitted due to missing information (n=55, data not shown).

Treated as a continuous variable in the fully-adjusted model, plasma tMg was inversely associated with mortality in cats with plasma tMg≤2.07 mg/dL (HR, 0.04; 95% CI, 0.01-0.27; P=0.001; n=57; mean tMg, 1.83 mg/dL). The association was nonlinear and nonsignificant in cats with tMg≥2.07 mg/dL (HR, 0.67; 95% CI, 0.24-1.85; P=0.438; n=65; mean tMg, 2.37 mg/dL). In the highest quartile, however, tMg was significantly associated with mortality (tMg≥2.26 mg/dL: HR, 0.12; 95% CI, 0.02-0.76; P=0.025; n=31, mean tMg, 2.62 mg/dL).

The pre-defined interaction between plasma magnesium concentration and phosphate status in association with all-cause mortality was explored with univariable Cox proportional hazards analysis. Cats that were hyperphosphatemic for IRIS stage at diagnosis of CKD (n=85) had increased risk of death (HR, 1.57; 95% CI, 1.13-2.16; P=0.007) compared to normophosphatemic cats (n=89). However, taking plasma magnesium concentration into account, only hyperphosphatemic cats with lower plasma magnesium had significant increased risk of death compared to normophosphatemic cats (NP-HM: HR, 0.53; 95% CI, 0.33-0.84; P=0.008, and NP-LM: HR, 0.51; 95% CI, 0.31-0.83; P=0.007), as well as to the hyperphosphatemic cats with higher plasma magnesium (HP-HM: HR, 0.60; 95% CI, 0.36-0.99; P=0.043). Compared to the NP-HM group as the joint reference category of no exposure, departure from additivity was observed with a relative excess risk of 0.79 in the HP-LM group, suggesting interaction between magnesium and phosphate in relation to survival (Table 5B).

TABLE 5

| | n | HR | 95% CI | P |
|---|---|---|---|---|
| A. Univariable results | | | | |
| Normomagnesemia | 143 | | | <0.001 |
| hypomagnesemia | 20 | 2.92 | 1.78-4.82 | <0.001 |
| hypermagnesemia | 11 | 2.88 | 1.54-5.38 | 0.001 |
| FGF-23 (<460 pg/mL) | 56 | | | <0.001 |
| 460-1800 pg/mL | 58 | 1.12 | 0.75-1.69 | 0.583 |
| >1800 pg/mL | 60 | 2.69 | 1.80-4.01 | <0.001 |
| Age (years) | 160 | 1.09 | 1.03-1.16 | 0.003 |
| Weight (<3.20 kg) | 57 | | | <0.001 |
| 3.21-4.15 kg | 57 | 0.57 | 0.38-0.84 | 0.005 |
| ≥4.16 kg | 56 | 0.40 | 0.26-0.60 | <0.001 |
| BCS (ideal weight) | 26 | | | 0.015 |
| underweight | 65 | 2.03 | 1.23-3.37 | 0.006 |
| overweight | 14 | 1.25 | 0.60-2.61 | 0.545 |
| Albumin (g/dL) | 174 | 0.38 | 0.22-0.67 | 0.001 |
| Creatinine (mg/dL) | 174 | 1.48 | 1.32-1.65 | <0.001 |
| PCV (%) | 172 | 0.91 | 0.88-0.94 | <0.001 |
| Phosphate (<4.00 mg/dL) | 57 | | | 0.001 |
| 4.00-5.26 mg/dL | 58 | 1.15 | 0.77-1.72 | 0.486 |
| ≥5.27 mg/dL | 59 | 2.09 | 1.41-3.10 | <0.001 |
| ln[PTH] (pg/mL) | 164 | 1.17 | 1.01-1.36 | 0.043 |
| Normotensive cats | 137 | | | |

TABLE 5-continued

| | n | HR | 95% CI | P |
|---|---|---|---|---|
| diagnosis of hypertension | 37 | 1.51 | 1.03-2.23 | 0.036 |
| USG (≤1.016) | 66 | | | 0.031 |
| 1.017-1.019 | 45 | 0.68 | 0.45-1.03 | 0.068 |
| ≥1.020 | 54 | 0.62 | 0.42-0.91 | 0.014 |
| UPC | 137 | 1.74 | 1.34-2.25 | <0.001 |
| Interactions with magnesium status | | | | |
| Creatinine (mg/dL) | | | | 0.019 |
| normomagnesemia | 143 | 1.82 | 1.47-2.24 | <0.001 |
| hypomagnesemia | 20 | 1.23 | 0.97-1.56 | 0.092 |
| hypermagnesemia | 11 | 1.69 | 1.09-2.65 | 0.020 |
| UPC | | | | 0.030 |
| normomagnesemia | 115 | 1.62 | 1.18-2.23 | 0.003 |
| hypomagnesemia | 13 | 1.30 | 0.54-3.12 | 0.555 |
| hypermagnesemia | 9 | 6.13 | 1.13-33.29 | 0.036 |
| Multivariable model (n = 122) | | | | |
| Normomagnesemia | 101 | | | 0.017 |
| hypomagnesemia | 12 | 2.74 | 1.35-5.55 | 0.005 |
| hypermagnesemia | 9 | 1.66 | 0.74-3.70 | 0.221 |
| Age (years) | 119 | 1.18 | 1.08-1.28 | <0.001 |
| Creatinine (mg/dL) | 119 | 1.29 | 1.12- 1.49 | 0.001 |
| PCV (%) | 119 | 0.92 | 0.89-0.96 | <0.001 |
| UPC | 119 | 2.28 | 1.45-3.60 | <0.001 |
| B. Phosphate-magnesium groups | | | | |
| NP-HM | 46 | | | 0.025 |
| NP-LM | 42 | 0.97 | 0.61-1.53 | 0.887 |
| HP-HM | 41 | 1.14 | 0.71-1.80 | 0.592 |
| HP-LM | 35 | 1.90 | 1.19-3.04 | 0.008 |
| | | | RERI = 1.90 − 0.97 − 1.14 + 1 = 0.79 | |

Table 5. Time-invariant Cox regression results identifying baseline predictors of mortality in cats with azotemic CKD. A. Univariable and multivariable regression results of the main analysis. B. Univariable results of the subanalysis examining the pre-specified interaction between phosphate and magnesium. HR, hazard ratio; 95% CI, 95% confidence interval; FGF-23, fibroblast growth factor 23; BCS, body condition score; PCV, packed cell volume; PTH, parathyroid hormone; USG, urine specific gravity; UPC, urine protein to creatinine ratio; NP, normophosphatemic; HP, hyperphosphatemic; LM, lower plasma magnesium; HM, higher plasma magnesium; RERI, relative excess risk due to interaction.

Association of Plasma Total Magnesium with Progression of CKD

Eighty-one cats had sufficient follow-up data available to be included in the progression analysis, of which 29 cats (36%) showed progression of CKD within the first 12 months of diagnosis. A significantly higher proportion of hypomagnesemic cats had progressive CKD (Table 2). Hypomagnesemia was associated with increased odds of progressive disease in univariable logistic regression analysis, but the effect of magnesium lost significance after adjustment for additional variables. Only higher baseline plasma FGF-23 remained a significant predictor associated with risk of progressive CKD in the final regression model (Nagelkerke $R^2$, 0.21; Table 6). No statistically significant difference in risk of progression was observed between hyperphosphatemic and normophosphatemic cats (P=0.194), nor between the 4 phosphate-magnesium groups (P=0.628). Therefore, the effect of joint exposure of plasma magnesium and phosphate in relation to progressive CKD was not further explored.

TABLE 6

| Univariable analysis | n | OR (95% CI) | P |
|---|---|---|---|
| Normomagnesemia | 67 | | 0.010 |
| hypomagnesemia | 8 | 17.68 (2.04-153.59) | 0.009 |
| hypermagnesemia | 4 | 7.58 (0.74-7.48) | 0.088 |
| ln[FGF-23] (pg/mL) | 79 | 1.90 (1.29-2.80) | 0.001 |
| PCV (%) | 79 | 0.87 (0.79-0.96) | 0.004 |
| Creatinine (mg/dL) | 79 | 2.65 (1.26-5.56) | 0.010 |
| Phosphate (mg/dL) | 79 | 1.33 (1.01-1.74) | 0.043 |
| Albumin (g/dL) | 79 | 0.19 (0.04-0.95) | 0.043 |

Table 6. Univariable binary logistic regression results identifying predictors of progressive CKD within the first 12 months of diagnosis of azotemic CKD in cats. Only ln[FGF-23] remained an independent risk factor for progression with multivariable regression. OR, odds ratio; 95% CI, 95% confidence interval; FGF-23, fibroblast growth factor 23; PCV, packed cell volume.

Discussion

Results from the observational cohort demonstrate an inverse relationship between plasma tMg and plasma FGF-23 concentrations in cats with azotemic CKD. A significant independent association between hypomagnesemia and increased risk of all-cause mortality was observed. Insufficient evidence was found for an independent association between magnesium status and risk of progressive CKD. In additional analyses, a possible link between hypomagnesemia and systemic hypertension was identified, and the risk of death associated with hyperphosphatemia appeared mitigated by higher plasma tMg.

The distribution of magnesium disorders across the different stages of CKD found in the study was comparable to those reported before in a smaller number of cats.[3] Hypermagnesemia is thought to result from incapacity of the kidneys to filter sufficient magnesium,[35,36] and was mostly found in cats with severe renal dysfunction. Hypomagnesemia in CKD is thought to be secondary to impaired intestinal absorption or increased renal excretion of magnesium, with depletion of the bone and muscle reserves.[35,37-39] Urinary magnesium excretion appeared higher in cats with hypomagnesemia, which could suggest renal magnesium wasting as the underlying cause.[39,40] However, this was based on a small number of observations and the spot sample method used to assess FE of magnesium lacks accuracy in cats.[41] Hypomagnesemia was independently associated with systemic hypertension.

Magnesium plays an active role in vascular resistance via various mechanisms such as regulation of intracellular calcium concentration, nitric oxide production and vascular calcification.[42-51] The relationship between magnesium and blood pressure is well-known in human medicine,[39,52-57] and magnesium infusion in dogs resulted in a decrease in vascular resistance and SBP.[58] Hyperaldosteronism is commonly observed in azotemic cats with systemic hypertension,[59,60] and could be a possible link between hypomagnesemia and hypertension, because aldosterone stimulates urinary magnesium excretion,[61,62] whilst magnesium inhibits aldosterone release.[63,64] No information on plasma aldosterone concentration was available for cats included in this study. Hypokalemia and hypocalcemia have been associated with magnesium deficiency in cats, dogs, and humans,[98,65-68] but were not common concurrent findings in the cohort.

An inverse association of plasma tMg with FGF-23 was found in the population of cats with CKD, and has previously been identified in human CKD patients on hemodialysis.[69] Results from rodent studies suggest that plasma FGF-23 concentration is influenced by dietary magnesium intake,[30,31,70] and hemodialysis-patients receiving magnesium-containing laxatives or phosphate binders had lower serum FGF-23 concentrations than patients not receiving PO magnesium.[69,70] On the other hand, a study examining the effect of oral magnesium supplementation on serum calcification propensity in human CKD stage 3 and 4 patients reported no significant reduction in FGF-23 concentration.[72] The underlying mechanisms of the relationship between magnesium and FGF-23 remain to be elucidated, but it could be hypothesized that FGF-23 has an effect on renal magnesium handling, as it was also shown to regulate tubular phosphate,[73,74] calcium,[75] and sodium[76] reabsorption. Aldosterone stimulates FGF-23 expression by osteoblasts,[77] so alternatively hyperaldosteronism, either as the cause of or secondary to hypomagnesemia, possibly could contribute to higher circulating FGF-23.

Hypomagnesemia at diagnosis of azotemic CKD was an independent predictor of mortality in cats. No previous survival studies in cats with CKD assessed the effect of magnesium status,[5-7] although both hypomagnesemia and hypermagnesemia were associated with decreased survival in cats hospitalized in an intensive care unit.[78] Multiple observational studies in human CKD patients report a link between hypomagnesemia and increased mortality, both in hemodialysis-patients[25,28] and patients with non-dialysis-dependent CKD.[24,26] Moreover, the mortality risk associated with hyperphosphatemia appears modified by serum magnesium concentration in hemodialysis-patients.[27] Hyperphosphatemia is a well-recognized risk factor in feline CKD,[6,7] and the results suggest that higher magnesium mitigates the risk of death associated with hyperphosphatemia in cats. A possible explanation could be an inhibitory role of magnesium on phosphate-induced vascular calcification,[21] although only scant reports exist on soft tissue and vascular calcification in cats with CKD.[2,79,80] In addition, both phosphate and magnesium influence plasma FGF-23, which has been identified as an important prognostic factor in cats with CKD,[5] although it did not remain a significant predictor of survival in the analysis presented here. Baseline FGF-23 was not included in the above-mentioned survival models for humans with CKD. The higher risk of death associated with hypermagnesemia in cats was lost after adjustment for additional variables and was possibly caused by its predominance in end-stage CKD. It must be noted, however, that this result was based on a low number of observations, resulting in a wide 95% confidence interval.

Hypomagnesemia was a risk factor for progression of azotemia in the cats, but, similar to humans,[24] the association was lost in multivariable analysis. Furthermore, magnesium has been shown to suppress phosphate-induced damage to murine proximal tubular cells,[23] and the degree of renal function decline associated with hyperphosphatemia in human CKD patients.[23] Although the relationship between hyperphosphatemia and renal fibrosis is well-known in cats with CKD,[8,81-83] no evidence for an effect of hyperphosphatemia on progression, nor interaction between magnesium and phosphate in relation to progression of azotemia, was found in the present study. These analyses could have been impacted by the short survival time of cats with magnesium disturbances, as demonstrating progressive increases in plasma creatinine is more difficult when the follow-up period is short.

Plasma tMg was measured after enrollment of cats to the cohort so the selection process was blinded to the exposure of interest. However, only cats with information on plasma FGF-23 were selected. This potential source of bias was addressed by comparing baseline data of included and cats excluded because of missing information. The prevalence of hypomagnesemia and hypermagnesemia were possibly underestimated, because these frequencies were assessed on a single time point rather than in a given time interval, whilst cats with these disorders were characterized by higher risks of death.

The true effects of hypomagnesemia and hypermagnesemia on progression and survival may have been underestimated due to misclassification bias. First, grouping of cats in different magnesium categories based on a single baseline measurement could have introduced regression dilution bias. Baseline magnesium concentration is lower in human patients that will develop hypomagnesemia during the course of their CKD,[24] but in what manner plasma magnesium changes over time in cats with CKD is unknown. Second, tMg consist of 3 fractions: ionized, protein-bound, and complexed magnesium.[19] Ionized magnesium status was overestimated by tMg in feline renal transplant recipients and in cats with diabetes mellitus,[65,84] thus cats with ionized hypomagnesemia could have been included in the normomagnesemic category, which would introduce non-differential misclassification if the effects observed with low magnesium are due to ionized rather than tMg status. However, only 1% of body magnesium is located in the extracellular fluid and no consensus exists on whether measurement of tMg or biologically-active ionized magnesium best represents magnesium status, and there is no good agreement between these methods.[35,39,85] Although multivariable analyses were performed, the possibility of residual confounding cannot be eliminated, and incomplete information for vitamin D-metabolites, blood gasses, bone parameters, and plasma aldosterone concentration prohibited investigation of relationships between magnesium and these variables.

The study identified low plasma total magnesium to be associated with higher plasma FGF-23 concentrations and reduced survival in feline CKD, which is in agreement with results from studies exploring the relationships of tMg with FGF-23 and survival in humans with CKD.[24,26,28,69,71] These observations were made on client-owned cats from first opinion practice with naturally-occurring CKD, and should be relevant to other populations of pet cats. However, multiple observations were made on a relatively small cohort of cats, and the findings therefore require validation by other studies in different populations of cats. Sequential measurements of plasma tMg would allow longitudinal analysis of the associations explored in this study and would especially benefit assessment of the relationship between plasma magnesium and progression of azotemia. The findings do suggest that plasma magnesium should be added to the routine plasma biochemistry panel assessed in cats with CKD as this analyte adds prognostic information and helps to identify cats with marked bone-mineral disorders.

REFERENCES

1. Lulich J P, Osborne C A, Obrien T D, et al. Feline Renal-Failure—Questions, Answers, Questions. Comp Cont Educ Pract 1992; 14:127.
2. DiBartola S P, Rutgers H C, Zack P M, et al. Clinicopathologic findings associated with chronic renal disease in cats: 74 cases (1973-1984). Journal of the American Veterinary Medical Association 1987; 190:1196-1202.
3. Barber P J, Elliott J. Feline chronic renal failure: calcium homeostasis in 80 cases diagnosed between 1992 and 1995. The Journal of small animal practice 1998; 39:108-116.
4. Geddes R F, Finch N C, Elliott J, et al. Fibroblast growth factor 23 in feline chronic kidney disease. Journal of veterinary internal medicine/American College of Veterinary Internal Medicine 2013; 27:234-241.
5. Geddes R F, Elliott J, Syme H M. Relationship between Plasma Fibroblast Growth Factor-23 Concentration and Survival Time in Cats with Chronic Kidney Disease. Journal of veterinary internal medicine/American College of Veterinary Internal Medicine 2015; 29:1494-1501.
6. King J N, Tasker S, Gunn-Moore D A, et al. Prognostic factors in cats with chronic kidney disease. Journal of veterinary internal medicine/American College of Veterinary Internal Medicine 2007; 21:906-916.
7. Boyd L M, Langston C, Thompson K, et al. Survival in cats with naturally occurring chronic kidney disease (2000-2002). Journal of veterinary internal medicine/American College of Veterinary Internal Medicine 2008; 22:1111-1117.
8. Chakrabarti S, Syme H M, Elliott J. Clinicopathological variables predicting progression of azotemia in cats with chronic kidney disease. Journal of veterinary internal medicine/American College of Veterinary Internal Medicine 2012; 26:275-281.
9. Goldman R, Bassett S H. Phosphorus Excretion in Renal Failure. Journal of Clinical Investigation 1954; 33:1623-1628.
10. Slatopolsky E. The intact nephron hypothesis: the concept and its implications for phosphate management in CKD-related mineral and bone disorder. Kidney international Supplement 2011:S3-8.
11. Isakova T, Wahl P, Vargas G S, et al. Fibroblast growth factor 23 is elevated before parathyroid hormone and phosphate in chronic kidney disease. Kidney Int 2011; 79:1370-1378.
12. Moe S, Drueke T, Cunningham J, et al. Definition, evaluation, and classification of renal osteodystrophy: a position statement from Kidney Disease: Improving Global Outcomes (KDIGO). Kidney Int 2006; 69:1945-1953.
13. Geddes R F, Finch N C, Syme H M, et al. The role of phosphorus in the pathophysiology of chronic kidney disease. Journal of veterinary emergency and critical care 2013; 23:122-133.
14. Barber P J, Rawlings J M, Markwell P J, et al. Effect of dietary phosphate restriction on renal secondary hyperparathyroidism in the cat. The Journal of small animal practice 1999; 40:62-70.
15. Elliott J, Rawlings J M, Markwell P J, et al. Survival of cats with naturally occurring chronic renal failure: effect of dietary management. The Journal of small animal practice 2000; 41:235-242.
16. Ross S J, Osborne C A, Kirk C A, et al. Clinical evaluation of dietary modification for treatment of spontaneous chronic kidney disease in cats. Journal of the American Veterinary Medical Association 2006; 229:949-957.
17. Plantinga E A, Everts H, Kastelein A M, et al. Retrospective study of the survival of cats with acquired chronic renal insufficiency offered different commercial diets. The Veterinary record 2005; 157:185-187.
18. Geddes R F, Elliott J, Syme H M. The effect of feeding a renal diet on plasma fibroblast growth factor 23 concentrations in cats with stable azotemic chronic kidney disease. Journal of veterinary internal medicine/American College of Veterinary Internal Medicine 2013; 27:1354-1361.
19. Jahnen-Dechent W, Ketteler M. Magnesium basics. Clinical kidney journal 2012; 5:i3-i14.
20. Sakaguchi Y, Hamano T, Nakano C, et al. Association between Density of Coronary Artery Calcification and Serum Magnesium Levels among Patients with Chronic Kidney Disease. PloS one 2016; 11:e0163673.
21. Louvet L, Buchel J, Steppan S, et al. Magnesium prevents phosphate-induced calcification in human aortic vascular smooth muscle cells. Nephrology, dialysis, transplantation: official publication of the European Dialysis and Transplant Association-European Renal Association 2013; 28:869-878.
22. Van Laecke S, Marechal C, Verbeke F, et al. The relation between hypomagnesaemia and vascular stiffness in renal transplant recipients. Nephrology, dialysis, transplantation: official publication of the European Dialysis and Transplant Association-European Renal Association 2011; 26:2362-2369.
23. Sakaguchi Y, Iwatani H, Hamano T, et al. Magnesium modifies the association between serum phosphate and the risk of progression to end-stage kidney disease in patients with non-diabetic chronic kidney disease. Kidney Int 2015.
24. Van Laecke S, Nagler E V, Verbeke F, et al. Hypomagnesemia and the risk of death and GFR decline in chronic kidney disease. The American journal of medicine 2013; 126:825-831.
25. Sakaguchi Y, Fujii N, Shoji T, et al. Hypomagnesemia is a significant predictor of cardiovascular and non-cardiovascular mortality in patients undergoing hemodialysis. Kidney Int 2014; 85:174-181.
26. Kanbay M, Yilmaz M I, Apetrii M, et al. Relationship between serum magnesium levels and cardiovascular events in chronic kidney disease patients. American journal of nephrology 2012; 36:228-237.
27. Sakaguchi Y, Fujii N, Shoji T, et al. Magnesium modifies the cardiovascular mortality risk associated with hyperphosphatemia in patients undergoing hemodialysis: a cohort study. PloS one 2014; 9:e116273.
28. Ishimura E, Okuno S, Yamakawa T, et al. Serum magnesium concentration is a significant predictor of mortality in maintenance hemodialysis patients. Magnesium research: official organ of the International Society for the Development of Research on Magnesium 2007; 20:237-244.
29. Iguchi A, Watanabe Y, Iino N, et al. Serum magnesium concentration is inversely associated with fibroblast growth factor 23 in haemodialysis patients. Nephrology 2014; 19:667-671.
30. Matsuzaki H, Kajita Y, Miwa M. Magnesium deficiency increases serum fibroblast growth factor-23 levels in rats. Magnesium research: official organ of the International Society for the Development of Research on Magnesium 2013; 26:18-23.
31. Matsuzaki H, Katsumata S, Maeda Y, et al. Changes in circulating levels of fibroblast growth factor 23 induced by short-term dietary magnesium deficiency in rats. Magnesium research: official organ of the International Society for the Development of Research on Magnesium 2016; 29:48-54.
32. Williams T L, Elliott J, Syme H M. Calcium and phosphate homeostasis in hyperthyroid cats: associations with development of azotaemia and survival time. The Journal of small animal practice 2012; 53:561-571.
33. Lefebvre H P, Dossin O, Trumel C, et al. Fractional excretion tests: a critical review of methods and applications in domestic animals. Veterinary clinical pathology/American Society for Veterinary Clinical Pathology 2008; 37:4-20.

34. de Mutsert R, Jager K J, Zoccali C, et al. The effect of joint exposures: examining the presence of interaction. Kidney Int 2009; 75:677-681.
35. Bateman S. Disorders of Magnesium: Magnesium Deficit and Excess. In: DiBartola S P, ed. Fluid, Electrolyte, and Acid-Base Disorders in Small Animal Practice. St. Louis, Mo.: Elsevier Saunders; 2012:212-229.
36. Navarro-Gonzalez J F, Mora-Fernandez C, Garcia-Perez J. Clinical implications of disordered magnesium homeostasis in chronic renal failure and dialysis. Seminars in dialysis 2009; 22:37-44.
37. Blaine J, Chonchol M, Levi M. Renal control of calcium, phosphate, and magnesium homeostasis. Clinical journal of the American Society of Nephrology: CJASN 2015; 10:1257-1272.
38. Barnes B A, Mendelson J. The measurement of exchangeable magnesium in dogs. Metabolism: clinical and experimental 1963; 12:184-193.
39. de Baaij J H, Hoenderop J G, Bindels R J. Magnesium in man: implications for health and disease. Physiological reviews 2015; 95:1-46.
40. Pham P C, Pham P A, Pham S V, et al. Hypomagnesemia: a clinical perspective. International journal of nephrology and renovascular disease 2014; 7:219-230.
41. Finco D R, Brown S A, Barsanti J A, et al. Reliability of using random urine samples for "spot" determination of fractional excretion of electrolytes in cats. American journal of veterinary research 1997; 58:1184-1187.
42. Touyz R M, Milne F J, Reinach S G. Intracellular Mg2+, Ca2+, Na2+ and K+ in platelets and erythrocytes of essential hypertension patients: relation to blood pressure. Clinical and experimental hypertension Part A, Theory and practice 1992; 14:1189-1209.
43. Kisters K, Krefting E R, Spieker C, et al. Increased Na+ and decreased Mg2+ intracellular concentrations in vascular smooth muscle cells from spontaneously hypertensive rats. Clinical science 1998; 95:583-587.
44. Yogi A, Callera G E, Antunes T T, et al. Vascular biology of magnesium and its transporters in hypertension. Magnesium research: official organ of the International Society for the Development of Research on Magnesium 2010; 23:S207-215.
45. Cunha A R, Medeiros F, Umbelino B, et al. Altered vascular structure and wave reflection in hypertensive women with low magnesium levels. Journal of the American Society of Hypertension: JASH 2013; 7:344-352.
46. Meema H E, Oreopoulos D G, Rapoport A. Serum magnesium level and arterial calcification in end-stage renal disease. Kidney Int 1987; 32:388-394.
47. Cheng P T, Grabher J J, LeGeros R Z. Effects of magnesium on calcium phosphate formation. Magnesium 1988; 7:123-132.
48. Pearson P J, Evora P R, Seccombe J F, et al. Hypomagnesemia inhibits nitric oxide release from coronary endothelium: protective role of magnesium infusion after cardiac operations. The Annals of thoracic surgery 1998; 65:967-972.
49. Satake K, Lee J D, Shimizu H, et al. Effects of magnesium on prostacyclin synthesis and intracellular free calcium concentration in vascular cells. Magnesium research: official organ of the International Society for the Development of Research on Magnesium 2004; 17:20-27.
50. Salem S, Bruck H, Bahlmann F H, et al. Relationship between Magnesium and Clinical Biomarkers on Inhibition of Vascular Calcification. American journal of nephrology 2012; 35:31-39.
51. Ishimura E, Okuno S, Kitatani K, et al. Significant association between the presence of peripheral vascular calcification and lower serum magnesium in hemodialysis patients. Clinical nephrology 2007; 68:222-227.
52. Joffres M R, Reed D M, Yano K. Relationship of magnesium intake and other dietary factors to blood pressure: the Honolulu heart study. The American journal of clinical nutrition 1987; 45:469-475.
53. Ma J, Folsom A R, Melnick S L, et al. Associations of serum and dietary magnesium with cardiovascular disease, hypertension, diabetes, insulin, and carotid arterial wall thickness: the ARIC study. Atherosclerosis Risk in Communities Study. Journal of clinical epidemiology 1995; 48:927-940.
54. Resnick L M, Bardicef O, Altura B T, et al. Serum ionized magnesium: relation to blood pressure and racial factors. American journal of hypertension 1997; 10:1420-1424.
55. Kass L, Weekes J, Carpenter L. Effect of magnesium supplementation on blood pressure: a meta-analysis. European journal of clinical nutrition 2012; 66:411-418.
56. Joosten M M, Gansevoort R T, Mukamal K J, et al. Urinary magnesium excretion and risk of hypertension: the prevention of renal and vascular end-stage disease study. Hypertension 2013; 61:1161-1167.
57. Geiger H, Wanner C. Magnesium in disease. Clinical kidney journal 2012; 5:i25-i38.
58. Nakayama T, Nakayama H, Miyamoto M, et al. Hemodynamic and electrocardiographic effects of magnesium sulfate in healthy dogs. Journal of veterinary internal medicine/American College of Veterinary Internal Medicine 1999; 13:485-490.
59. Jepson R E, Syme H M, Elliott J. Plasma renin activity and aldosterone concentrations in hypertensive cats with and without azotemia and in response to treatment with amlodipine besylate. Journal of veterinary internal medicine/American College of Veterinary Internal Medicine 2014; 28:144-153.
60. Jensen J, Henik R A, Brownfield M, et al. Plasma renin activity and angiotensin I and aldosterone concentrations in cats with hypertension associated with chronic renal disease. American journal of veterinary research 1997; 58:535-540.
61. Barr C S, Lang C C, Hanson J, et al. Effects of adding spironolactone to an angiotensin-converting enzyme inhibitor in chronic congestive heart failure secondary to coronary artery disease. The American journal of cardiology 1995; 76:1259-1265.
62. Sontia B, Montezano A C, Paravicini T, et al. Down-regulation of renal TRPM7 and increased inflammation and fibrosis in aldosterone-infused mice: effects of magnesium. Hypertension 2008; 51:915-921.
63. Ichihara A, Suzuki H, Saruta T. Effects of magnesium on the renin-angiotensin-aldosterone system in human subjects. The Journal of laboratory and clinical medicine 1993; 122:432-440.
64. Atarashi K, Matsuoka H, Takagi M, et al. Magnesium ion: A possible physiological regulator of aldosterone production. Life sciences 1989; 44:1483-1489.
65. Wooldridge J D, Gregory C R. Ionized and total serum magnesium concentrations in feline renal transplant recipients. Veterinary surgery: VS 1999; 28:31-37.
66. Kimmel S E, Waddell L S, Michel K E. Hypomagnesemia and hypocalcemia associated with protein-losing enteropathy in Yorkshire terriers: five cases (1992-1998). Journal of the American Veterinary Medical Association 2000; 217:703-706.

67. Huang C L, Kuo E. Mechanism of hypokalemia in magnesium deficiency. Journal of the American Society of Nephrology: JASN 2007; 18:2649-2652.
68. Yamamoto M, Yamaguchi T, Yamauchi M, et al. Acute-onset hypomagnesemia-induced hypocalcemia caused by the refractoriness of bones and renal tubules to parathyroid hormone. Journal of bone and mineral metabolism 2011; 29:752-755.
69. Iguchi A, Watanabe Y, Iino N, et al. Serum magnesium concentration is inversely associated with fibroblast growth factor 23 in haemodialysis patients. Nephrology 2014; 19:667-671.
70. van Angelen A A, San-Cristobal P, Pulskens W P, et al. The impact of dietary magnesium restriction on magnesiotropic and calciotropic genes. Nephrology, dialysis, transplantation: official publication of the European Dialysis and Transplant Association-European Renal Association 2013; 28:2983-2993.
71. Covic A, Passlick-Deetjen J, Kroczak M, et al. A comparison of calcium acetate/magnesium carbonate and sevelamer-hydrochloride effects on fibroblast growth factor-23 and bone markers: post hoc evaluation from a controlled, randomized study. Nephrology, dialysis, transplantation: official publication of the European Dialysis and Transplant Association-European Renal Association 2013; 28:2383-2392.
72. Bressendorff I, Hansen D, Schou M, et al. Oral Magnesium Supplementation in Chronic Kidney Disease Stages 3 and 4: Efficacy, Safety, and Effect on Serum Calcification Propensity—A Prospective Randomized Double-Blinded Placebo-Controlled Clinical Trial. Kidney International Reports 2017; 2:380-389.
73. Andrukhova O, Zeitz U, Goetz R, et al. FGF23 acts directly on renal proximal tubules to induce phosphaturia through activation of the ERK1/2-SGK1 signaling pathway. Bone 2012; 51:621-628.
74. Shimada T, Urakawa I, Yamazaki Y, et al. FGF-23 transgenic mice demonstrate hypophosphatemic rickets with reduced expression of sodium phosphate cotransporter type IIa. Biochemical and biophysical research communications 2004; 314:409-414.
75. Andrukhova O, Smorodchenko A, Egerbacher M, et al. FGF23 promotes renal calcium reabsorption through the TRPV5 channel. The EMBO journal 2014; 33:229-246.
76. Andrukhova O, Slavic S, Smorodchenko A, et al. FGF23 regulates renal sodium handling and blood pressure. EMBO molecular medicine 2014; 6:744-759.
77. Zhang B, Umbach A T, Chen H, et al. Up-regulation of FGF23 release by aldosterone. Biochemical and biophysical research communications 2016; 470:384-390.
78. Toll J, Erb H, Birnbaum N, et al. Prevalence and incidence of serum magnesium abnormalities in hospitalized cats. Journal of veterinary internal medicine/American College of Veterinary Internal Medicine 2002; 16:217-221.
79. Barber P J. Parathyroid gland function in the ageing cat [PhD Thesis]. In: Royal Veterinary College. London: University of London; 1998:289.
80. McLeland S M, Lunn K F, Duncan C G, et al. Relationship among serum creatinine, serum gastrin, calcium-phosphorus product, and uremic gastropathy in cats with chronic kidney disease. Journal of veterinary internal medicine/American College of Veterinary Internal Medicine 2014; 28:827-837.
81. Ross L A, Finco D R, Crowell W A. Effect of dietary phosphorus restriction on the kidneys of cats with reduced renal mass. American journal of veterinary research 1982; 43:1023-1026.
82. Chakrabarti S, Syme H M, Brown C A, et al. Histomorphometry of feline chronic kidney disease and correlation with markers of renal dysfunction. Veterinary pathology 2013; 50:147-155.
83. Lawson J, Elliott J, Wheeler-Jones C, et al. Renal fibrosis in feline chronic kidney disease: known mediators and mechanisms of injury. Veterinary journal 2015; 203:18-26.
84. Norris C R, Nelson R W, Christopher M M. Serum total and ionized magnesium concentrations and urinary fractional excretion of magnesium in cats with diabetes mellitus and diabetic ketoacidosis. Journal of the American Veterinary Medical Association 1999; 215:1455-1459.
85. Elfin R J. Assessment of magnesium status for diagnosis and therapy. Magnesium research: official organ of the International Society for the Development of Research on Magnesium 2010; 23:S194-198.
86. Gonella M, Ballanti P, Della Rocca C, et al. Improved bone morphology by normalizing serum magnesium in chronically hemodialyzed patients. Mineral and electrolyte metabolism 1988; 14:240-245.
87. Turgut F, Kanbay M, Metin M R, et al. Magnesium supplementation helps to improve carotid intima media thickness in patients on hemodialysis. International urology and nephrology 2008; 40:1075-1082.
88. International Renal Interest Society Guidelines: IRIS Staging of CKD. http://iris-kidney.com/guidelines/staging.html
89. Parks Electronic Doppler Model 811B; Perimed U K, Bury St Edmunds, U K.
90. Idexx laboratories, Wetherby, UK.
91. FGF-23 ELISA Kit, Kainos Laboratories, Tokyo, Japan.
92. Total intact PTH immunoradiometric assay—coated bead version, 3KG600, Scantibodies, Santee, Calif., USA.
93. iSTAT 1 point-of-care analyzer, Abbott Point of Care Inc., Princeton, N.J., USA.
94. Michigan State University Diagnostic Center for Population and animal Health, Lansing, Mich.
95. IBM SPSS Statistics for Windows, Version 24, IBM Corp., Armonk, N.Y., USA and GraphPad Prism 7, GraphPad Software, La Jolla, Calif., USA.
96. International Renal Interest Society Guidelines: Treatment Recommendations for CKD in Cats (2015). http://www.iris-kidney.com/guidelines/recommendations.html
97. REM=HRHP-LM−HRNP-LM−HRHP-HM+1
98. Dupha N. Serum magnesium abnormalities in a small animal intensive care unit population. J Vet Intern Med 1994; 8: 157 (abstract).

Although the presently disclosed subject matter and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein can be utilized according to the presently disclosed subject matter. Accordingly, the appended claims are intended to include within their scope such processes, machines, manufacture, compositions of matter, means, methods, or steps.

Patents, patent applications, publications, product descriptions and protocols are cited throughout this application the disclosures of which are incorporated herein by reference in their entireties for all purposes.

What is claimed is:

1. A method of diagnosing and treating an animal at risk for chronic kidney disease (CKD), wherein the method comprises:
   a. obtaining a blood sample from the animal;
   b. determining an amount of magnesium in the blood sample of the animal;
   c. comparing the amount of magnesium to predetermined reference values; wherein the predetermined reference values are based on average magnesium levels in blood in a control population;
   d. diagnosing the animal as being at risk for the CKD if the amount of magnesium is below a first predetermined value or above a second predetermined reference value; and
   e. providing the animal with a treatment regimen if the amount of magnesium is below a first predetermined value or above a second predetermined reference value, wherein the treatment regimen comprises:
      (i) at least one treatment regimen selected from the group consisting of administering a composition comprising an effective amount of magnesium or a salt thereof, reducing phosphate intake, reducing protein intake, administering polyunsaturated fatty acids, administering a phosphate binder therapy, administering potassium, reducing dietary sodium intake, and combinations thereof, or
      (ii) at least one treatment regimen selected from the group consisting of a dietary therapy, hemodialysis, renal replacement therapy, withdrawal of kidney damaging compounds, kidney transplantation, delaying or avoiding kidney damaging procedures, modifying diuretic administration, and combinations thereof.

2. The method of claim 1, further comprising the steps of determining an amount of FGF23 in the blood sample of the animal; comparing the amount of FGF23 to a third predetermined reference value; and wherein the predetermined reference value is based on an average FGF23 level in blood in a control population, and wherein a higher FGF23 level compared to the second predetermined reference value indicates a higher likelihood of effective treatment.

3. The method of claim 1, wherein the treatment regimen comprises at least one treatment regimen selected from the group consisting of administering a composition comprising an effective amount of magnesium or a salt thereof, reducing phosphate intake, reducing protein intake, administering polyunsaturated fatty acids, administering a phosphate binder therapy, administering potassium, reducing dietary sodium intake, and combinations thereof.

4. The method of claim 1, wherein the treatment regimen comprises at least one treatment regimen selected from the group consisting of a dietary therapy, hemodialysis, renal replacement therapy, withdrawal of kidney damaging compounds, kidney transplantation, delaying or avoiding kidney damaging procedures, modifying diuretic administration, and combinations thereof.

5. The method of claim 1, further comprising:
   a. determining an amount of at least one further biomarker selected from the group consisting of phosphate, creatinine, blood urine nitrogen (BUN) and parathyroid hormone (PTH) in the blood sample, and
   b. comparing the amount of the at least one further biomarker to a fourth predetermined reference value, wherein the amount of phosphate, creatinine, blood urine nitrogen (BUN) and/or parathyroid hormone (PTH) being above the fourth predetermined reference value indicates a higher likelihood of effective treatment.

6. The method of claim 2, further comprising maintaining the animal on the composition for a sufficient period of time to reduce the amount of FGF23 in the animal.

7. The method of claim 1, wherein the amount of magnesium in the blood sample is less than about 50% of the average amount of magnesium in blood in a control population.

8. The method of claim 1, wherein the amount of FGF23 or the further biomarkers in the blood sample is at least about 150% of the average amount of FGF23 or the further biomarkers in blood in a control population.

9. The method of claim 1, further comprising determining blood pressure of the animal, comparing the blood pressure to a fifth predetermined reference value, and administrating a prevention or treatment regimen of hypertension if the blood pressure is higher than the fifth predetermined reference value.

10. The method of claim 9, wherein the blood pressure is a systolic pressure or a diastolic pressure.

11. The method of claim 3, wherein the magnesium is in a magnesium coordination complex.

12. The method of claim 3, wherein the treatment regimen is administering a composition comprising an effective amount of magnesium or a salt thereof.

13. The method of claim 12, wherein the amount of magnesium ranges from about 50 mg/1000 Kcal to about 500 mg/1000 Kcal.

14. The method of claim 12, wherein the composition comprising magnesium is provided to the animal at least once a day.

15. The method of claim 1, wherein the animal is a companion animal a dog or a cat.

* * * * *